(12) United States Patent
Dobak, III

(10) Patent No.: US 7,551,964 B2
(45) Date of Patent: Jun. 23, 2009

(54) SPLANCHNIC NERVE STIMULATION FOR TREATMENT OF OBESITY

(75) Inventor: John D. Dobak, III, La Jolla, CA (US)

(73) Assignee: Leptos Biomedical, Inc., Fridley, MN (US)

( * ) Notice: Subject to any disclaimer, the term of this patent is extended or adjusted under 35 U.S.C. 154(b) by 440 days.

(21) Appl. No.: 10/785,726

(22) Filed: Feb. 24, 2004

(65) Prior Publication Data

US 2004/0230255 A1    Nov. 18, 2004

Related U.S. Application Data

(63) Continuation-in-part of application No. 10/272,430, filed on Oct. 16, 2002, now Pat. No. 7,236,822, which is a continuation-in-part of application No. 10/243,612, filed on Sep. 13, 2002, now Pat. No. 7,239,912.

(60) Provisional application No. 60/366,750, filed on Mar. 22, 2002, provisional application No. 60/370,311, filed on Apr. 5, 2002, provisional application No. 60/379,605, filed on May 10, 2002, provisional application No. 60/384,219, filed on May 30, 2002, provisional application No. 60/386,699, filed on Jun. 10, 2002, provisional application No. 60/450,534, filed on Feb. 25, 2003, provisional application No. 60/452,361, filed on Mar. 5, 2003, provisional application No. 60/466,890, filed on Apr. 30, 2003, provisional application No. 60/466,805, filed on Apr. 30, 2003, provisional application No. 60/479,933, filed on Jun. 19, 2003, provisional application No. 60/496,437, filed on Aug. 20, 2003.

(51) Int. Cl.
A61N 1/36    (2006.01)

(52) U.S. Cl. .................. 607/40; 607/2; 607/58

(58) Field of Classification Search .............. 607/2, 607/58, 40
See application file for complete search history.

(56) References Cited

U.S. PATENT DOCUMENTS 3,911,930 A    10/1975    Hagfors et al.

(Continued)

FOREIGN PATENT DOCUMENTS

WO    WO 98/57701 A1    12/1998

(Continued)

OTHER PUBLICATIONS

Kurose, T. et al., *Gulcagon, insulin and somatostatin secretion in response to sympathetic neuralactivation in streptozotocin-induced diabetic rats. A study with the isolatedperfused rat pancreas in vitro.* Diabetologia Nov. 1992; 35(11): 1035-41.

(Continued)

*Primary Examiner*—Carl H Layno
*Assistant Examiner*—Yun Haeng Lee
(74) *Attorney, Agent, or Firm*—Craig F. Taylor; James W. Hill

(57) ABSTRACT

A method for the treatment of obesity or other disorders by electrical activation or inhibition of the sympathetic nervous system is disclosed. This activation or inhibition can be accomplished by stimulating the greater splanchnic nerve or other portion of the sympathetic nervous system using an electrode. This nerve activation can result in reduced food intake and increased energy expenditure.

21 Claims, 12 Drawing Sheets

(Weight of single animal from each of Cohort 1 and Cohort 2 where the stimulator was turned off divided by the average weight of the three Control animals.)

U.S. PATENT DOCUMENTS

| | | | |
|---|---|---|---|
| 4,573,481 A | 3/1986 | Bullara | |
| 4,595,010 A | 6/1986 | Radke | |
| 4,827,935 A | 5/1989 | Geddes et al. | |
| 4,867,164 A | 9/1989 | Zabara | |
| 5,095,905 A | 3/1992 | Klepinski | |
| 5,107,833 A | 4/1992 | Barsness | |
| 5,154,172 A | 10/1992 | Terry, Jr. et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,205,285 A | 4/1993 | Baker, Jr. | |
| 5,215,086 A | 6/1993 | Terry, Jr. et al. | |
| 5,215,089 A | 6/1993 | Baker, Jr. | |
| 5,222,494 A | 6/1993 | Baker, Jr. | |
| 5,231,988 A | 8/1993 | Wernicke et al. | |
| 5,235,980 A | 8/1993 | Varrichio et al. | |
| 5,237,991 A | 8/1993 | Baker, Jr. et al. | |
| 5,251,634 A | 10/1993 | Weinberg | |
| 5,263,480 A | 11/1993 | Wernicke et al. | |
| 5,269,303 A | 12/1993 | Wernicke et al. | |
| 5,299,569 A | 4/1994 | Wernicke et al. | |
| 5,304,206 A | 4/1994 | Baker, Jr. et al. | |
| 5,330,515 A | 7/1994 | Rutecki et al. | |
| 5,335,657 A | 8/1994 | Terry, Jr. et al. | |
| 5,351,394 A | 10/1994 | Weinberg | |
| 5,423,872 A | 6/1995 | Cigaina | |
| 5,454,840 A | 10/1995 | Krakovsky et al. | |
| 5,458,626 A | 10/1995 | Krause | |
| 5,531,778 A | 7/1996 | Maschino et al. | |
| 5,540,730 A | 7/1996 | Terry, Jr. et al. | |
| 5,540,734 A | 7/1996 | Zabara | |
| 5,571,150 A | 11/1996 | Wernicke et al. | |
| 5,690,691 A | 11/1997 | Chen et al. | |
| 5,707,400 A | 1/1998 | Terry, Jr. et al. | |
| 5,716,392 A | 2/1998 | Bourgeois et al. | |
| 5,725,563 A | 3/1998 | Klotz | |
| 5,755,750 A | 5/1998 | Petruska et al. | |
| 5,782,798 A | 7/1998 | Rise | |
| 5,836,994 A | 11/1998 | Bourgeois | |
| 5,861,014 A | 1/1999 | Familoni | |
| 5,919,216 A | 7/1999 | Houben et al. | |
| 5,928,272 A | 7/1999 | Adkins et al. | |
| 5,995,872 A | 11/1999 | Bourgeois | |
| 6,041,258 A | 3/2000 | Cigaina | |
| 6,068,596 A | 5/2000 | Weth et al. | |
| 6,109,269 A | 8/2000 | Rise et al. | |
| 6,129,685 A | 10/2000 | Howard, III | |
| 6,146,391 A | 11/2000 | Cigaina | |
| 6,165,180 A | 12/2000 | Cigaina | |
| 6,169,924 B1 | 1/2001 | Meloy et al. | |
| 6,308,105 B1 | 10/2001 | Duysens et al. | |
| 6,321,124 B1 | 11/2001 | Cigaina | |
| 6,350,455 B1 | 2/2002 | Donovan | |
| 6,356,786 B1 | 3/2002 | Rezai et al. | |
| 6,356,787 B1 | 3/2002 | Rezai et al. | |
| 6,381,495 B1 | 4/2002 | Jenkins | |
| 6,438,423 B1 | 8/2002 | Rezai et al. | |
| 6,497,718 B1 | 12/2002 | Dewan | |
| 6,558,320 B1 | 5/2003 | Causey et al. | |
| 6,587,719 B1 | 7/2003 | Barrett et al. | |
| 6,721,603 B2 | 4/2004 | Zabara et al. | |
| 6,885,888 B2 | 4/2005 | Rezai | |
| 6,912,419 B2 | 6/2005 | Hill et al. | |
| 7,076,292 B2 | 7/2006 | Forsberg | |
| 7,155,278 B2 | 12/2006 | King et al. | |
| 2001/0014815 A1 | 8/2001 | Matsumura et al. | |
| 2002/0072780 A1 | 6/2002 | Foley | |
| 2002/0077675 A1 | 6/2002 | Greenstein | |
| 2002/0099419 A1* | 7/2002 | Cohen et al. | 607/46 |
| 2003/0018367 A1* | 1/2003 | DiLorenzo | 607/46 |
| 2003/0045909 A1 | 3/2003 | Gross et al. | |
| 2003/0144708 A1 | 7/2003 | Starkebaum | |
| 2003/0181958 A1 | 9/2003 | Dobak, III | |
| 2004/0230255 A1 | 11/2004 | Dobak, III | |
| 2005/0143788 A1 | 6/2005 | Yun et al. | |
| 2005/0149146 A1 | 7/2005 | Boveja et al. | |

FOREIGN PATENT DOCUMENTS

| | | |
|---|---|---|
| WO | WO 00/61223 A1 | 10/2000 |
| WO | WO 01/52932 A1 | 7/2001 |
| WO | WO 01/58520 A1 | 8/2001 |
| WO | WO 01/83028 A1 | 11/2001 |
| WO | WO 02/04068 A1 | 1/2002 |
| WO | WO 02/26315 A1 | 4/2002 |
| WO | WO 02/26317 A1 | 4/2002 |
| WO | WO 02/34331 A2 | 5/2002 |
| WO | WO 02/43467 A2 | 6/2002 |
| WO | WO 02/062291 A2 | 8/2002 |

OTHER PUBLICATIONS

Kaneto, A., et al., *Effect of splanchnic nerve stimulation on glucagons and insulin output in the dog*, Endocrinolgy Jan. 1975; 96(1): 143-50.

Opsahl, Charles A., *Department of Psychology*, Yale University, New Haven Connecticut 06520, Jul. 7, 1976, "Sympathetic nervous system involvement in the lateral hypothalamic lesion syndrome."

Itina, L.V., *Sechenov Physiological Journal of the USSR, Institute of Physiology Acad. Sci.* Belorus. SSR, Minsk, 1979, "Sympathoactivatory and sympatho-inhibitory afferent fibers of vagus and splanchnic nerves." (Russian text with English abstract).

Itina, L.V., et al., *Sechnov Physiological Journal of the USSR, Institute of Physiology Acad. Sci.* BSSR, Minsk, 1972, "Impulsation of the splanchnic and vagus nerves after introduction of fat into the lumen of the small intestine." (Russian text with English abstract).

Shimazu, T., *Diabetologia*, (1981) 20: 343-356, "Central Nervous System Regulation of Liver and Adipose Tissue Metabolism."

Rozman, J., et al., *National Library of Medicine; Physiol Meas.*, Nov. 2002; 23(4):695-705, "Recording of ENGs from the nerves innervating the pancreas of a dog during the intravenous glucose tolerance test."

Ahren, B., *Diabetologia*, (2000) 43: 393-410, "Autonomic regulation of islet hormone secretion—Implications for health and disease."

Bolte, E. et al., "Steroid Production from Plasma Cholesterol. II In Vivo Conversion of Plasma Cholesterol to Ovarian Progesterone and Adrenal C10 and C21 Steroids in Humans", JCE&M, vol. 38, No. 3,(1974), pp. 394-400.

Chen, KE et al., "Induction of Leptin Resistance Through Direct Interaction of C-Reactive Protein with Leptin", Nature Medicine, vol. 12, No. 4,(2006), pp. 425-432.

Clutter, William E., "Epinephrine Plasma Metabolic Clearance Rates and Physiologic Thresholds for Metabolic and Hemodynamic Actions in Man", Journal of Clinic Investigations, vol. 66,(1980), pp. 94-101.

Mirkin, Bernard L., "Factors Influencing the Selective of Adrenal Medullary Hormones", Journal Pharmacol. Exp. Ther., vol. 132,(1960), pp. 218-225.

Ravussin, Eric "Reduced Rate of Energy Expenditure as a Risk Factor for Body-Weight Gain", New England Journal of Medicine, vol. 318,(1988), pp. 467-472.

Staten, M. A., "Physiological Increments in Epinephrine Stimulate Metabolic Rate in Humans", Am. J. Physiol., vol. 253,(Nov. 1986), pp. 322-330.

Tataranni, P. "From Physiology to Neuroendocrinology: A Reappraisal of Risk Factors of Body Weight Gain in Humans", Diabetes and Metabolism, vol. 24 No. 2,(1998), pp. 108-115.

Mokdad, A "The Continuing Epidemics of Obesity and Diabetes in the United States", Journal of the American Medical Association, vol. 286, No. 10, (Sep. 2001), pp. 1195-1200.

Sjostrom, L "Epinephrine Sensitivity with respect to Metabolic Rate and Other Variables in Women", American Journal of Physiology, vol. 245., (Sep. 1982), pp. E431-E442.

Katzeff, H "Metabolic Studies in Human Obesity during Overnutrition and Undernutrition: Thermogenic and Hormonal Responses to Norepinephrine, Metabolism", vol. 35, No. 2., (Feb. 1986), pp. 166-175.

Leibel, R. "Changes in Energy Expenditure Resulting from Altered Body Weight", The New England Journal of Medicine, vol. 332, No. 10., (Mar. 1995), pp. 621-628.

Matthews, D. "Effect of Epinephrine on Amino Acid and Energy Metabolism in Humans", American Journal of Physiology, vol. 258., (Sep. 1989), pp. E948-E956.

Ratheiser, K. "Epinephrine Produces a Prolonged Elevation in Metabolic Rate in Humans", American Journal of Nutrition, vol. 68, (Oct. 1997), pp. 1046-1052.

Effects of Vasoactive Drugs on Circulation in Canine Subcutaneous Adipose Tissue., B.B. Fredholm, *Acta Physiol. Scand.* 1970, 79. 564-574.

Gastric Distension Modulates Hypthalamic Neurons Via a Sympathetic Afferent Path Through the Mesencephalic Periaqueductal Gray., Frank C. Barone, Irma Zarco De Coronado and Matthew J. Wayner, *Brain Research Bulletin*, vol. 38, No. 3, pp. 239-251, 1995.

Recording of Electroneurograms from the Nerves Innervating the Pancreas of a Dog., Janez Rosman, B. Zorko, and M. Bunc, *Journal of Neuroscience Methods 112* (2001) 155-162.

Influence of Electrical Supramedullary Stimulation on the Plasma Level of Free Fatty Acids, Blood Pressure and Heart Rate in the Dog., Lars Orö, Lars R. Wallenberg and Per Bolme, *Acta Medica Scandinavica*. vol. 178, fasc. 6, 1965.

The Subcutaneous Lipolytic Response to Regional Neural Stimulation is Reduced in Obese Women., Christoph Dodt, Peter Lönnroth, Horst Lorenz, and Mikael Elam, *Diabetes*, vol. 49, Nov. 2000.

Direct Evidence for Tonic Sympathetic Support of Resting Metabolic Rate in Healthy Adult Humans., Mary Beth Monroe, Douglas R. Seals, Linda F. Shapiro, Christopher Bell, David Johnson, and Pamela Parker Jones., *Am. J. Physiol Endocrinol Metab. 280: E740-E744*, 2001.

Intraneural Stimulation Elicits an Increase in Subcutaneous Interstitial Glycerol Levels in Humans, Christoph Dodt, Peter Lönroth, Horst Lorenz Fehm, and Mike Elam., *Journal of Physiology* (1999), 521.2, pp. 545-552.

Release of Free Fatty Acids From Subcutaneous Adipose Tissue in Dogs Following Sympathetic Nerve Stimulation., S. Rosell, *Acta Physiol. Scan.* 1966. 67. 343-351.

The Unresponsiveness of Lipid Metabolism in Canine Mesenteric Adipose Tissue to Biogenic Amines and to Sympathetic Nerve Stimulation., Kathryn Ballard and Sune Rosell., *Acta Physiol. Scan.* 1969. 77. 442-448.

Sympathetic Control of White Adipose Tissue in Lean and Obese Humans., C. Dodt, P. Lönnroth, J.P. Wellhöner, H.L. Felm, and M. Elam, *Acta Physiol. Scan.* 2003, 177, 351-357.

Stimulation of Nerves Innervating the Dog's Pancreas., Janez Rozman, Bojan Zorko, Matjaz Bunc, and Mojca Zitko., *Artificial Organs* 26(3); 241-243, (2002).

Bray, *Reciprocal relation of food intake and sympathetic activity: experimental observations and clinical implications*, International Journal of Obesity (2000) 24, Suppl 2, S8-S17.

Jarhult, M.D., et al., *The Functional Importance of Sympathetic Nerves to the Liver and Endocrine Pancreas*, Ann. Surg., Jan. 1979, vol. 189, No. 1, p. 96-100.

Pan, et al., *Role of Summation of Afferent Input in Cardiovascular Reflexes from Splanchnic Nerve Stimulation*, The American Physiological Society, (1996) pp. H849-H856.

Jorum, et al., *Analgesia by low-frequency nerve stimulation mediated by low-threshold afferents in rats*, Pain, 32 (1988) 357-366.

Van Den Honert, et al., *Generation of Unidirectionally Propagated Action Potentials in a Peripheral Nerve by Brief Stimuli*, Science, vol. 206, Dec. 14, 1979, pp. 1311-1312.

Van Den Honert, et al., *A Technique for Collision Block of Peripheral Nerve: Single Stimulus Analysis*, IEEE Transactions on Biomedical Engineering, vol. BME-28, No. 5, May 1981, pp. 373-378.

Rozman, et al., *Multielectrode Spiral Cuff for Selective Stimulation of Nerve Fibres*, Journal of Medical Engineering & Technology, vol. 16, No. 5, (Sep./Oct. 1992), pp. 194-203.

Crago, et al., *The Choice of Pulse Duration for Chronic Electrical Stimulation via Surface, Never, and Intramuscular Electrodes*, Annals of Biomedical Engineering, 2, (1974), pp. 252-264.

Jonson, et al., *Splanchnic Nerve Stimulation Inhibits Duodenal HCO3 Secretion in the Rat*, American Physiological Society, (1988), pp. G709-G712.

Edwards, et al., *The Effect of Splanchnic Nerve Stimulation on the Uptake of Atrial Natriuretic Peptide by the Adrenal Gland in Conscious Calves*, J. Endocrinol. Invest. 13, (1990), pp. 887-892.

Edwards, et al., *Adrenal Medullary Responses to Stimulation of the Splanchnic Nerve in the Conscious Calf*, J. Physiol (1980), 308, pp. 15-27.

Alamo, et al., *Electrically-Evoked Catecholamine Release from Cat Adrenals*, Biochemical Pharmacology, (1991), vol. 42, No. 5, pp. 973-978.

Stoddard, et al., *Adrenal Medullary Secretion with Splanchnic Stimulation in Spinal Cats*, Journal of the Autonomic Nervous System, 38 (1992), pp. 105-116.

Edwards, et al., *The Effect of Splanchnic Nerve Stimulation on Adrenocortical Activity in Conscious Calves*, J. Physiol, (1987) 382, pp. 385-396.

Edwards, A.V., *Adrenal Catecholamine Output in Response to Stimulation of the Splanchnic Nerve in Bursts in the Conscious Calf*, J. Physiol, (1982) 327, pp. 409-419.

Buckley, et al., *Circulatory Effects of Splanchnic Nerve Stimulation in Developing Swine*, The American Physiological Society, (1996), pp. H69-H74.

Edwards, A.V., *The Glycogenolytic Response to Stimulation of the Splanchnic Nerves in Adrenalectomized Calves, Sheep, Dogs, Cats and Pigs*, J. Physiol, (1971) 213, pp. 741-759.

Edwards, A.V., *The Sensitivity of the Hepatic Gylcogenolytic Mechanism to Stimulation of the Splanchnic Nerves*, J. Physiol (1972), 220, pp. 315-334.

Dunning, et al., *Pancreatic and Extrapancreatic Galanin Release During Sympathetic Neural Activiation*, Am J Physiol Endocrinol Metab, Mar. 1990; 258: pp. 436-444.

Ahren, et al., *Sympathetic Nerve Stimulation Versus Pancreatic Norepinephrine Infusion In the Dog: 1) Effects on Basal Release of Insulin and Glucagon*, Endorinology, vol. 121, No. 1, pp. 323-331, 1987.

Kurose, et al., *Mechanism of Sympathetic Neural Regulation of Insulin, Somatostatin, and Glucagon Secretion*, American Physiological Society, (1990) pp. E220-E227.

Holst, et al., *Nervous Control of Pancreatic Exocrine Secretion in Pigs*, Acta Physiol Scand., (1979) 105, pp. 33-51.

Cigaina, et al., *Long-Term Effects of Gastric Pacing to Reduce Feed Intake in Swine*, Obesity Surgery, 6, (1996), pp. 250-253.

Cigaina, et al., *Gastric Peristalsis Control by Mono Situ Electrical Stimulation: a Preliminary Study*, Obesity Surgery, 6, (1996), pp. 247-249.

Birks, R.I., *Regulation by Patterned Preganglionic Neural Activity of Transmitter Stores in a Sympathetic Ganglion*, J. Physiol., (1978), 280, pp. 559-572.

Friesen, et al., *Canadian Journal of Physiology and Pharmacology*, The National Research Council of Canada, vol. 49, May 1971, No. 5, pp. 375-381.

Brown, et al., *Changes in Food Intake with Electrical Stimulation of the Ventromedial Hypothalamus in Dogs*, J Neurosurg, vol. 60, Jun. 1984, pp. 1253-1257.

Woodbury, et al., *Effects of Vagal Stimulation on Experimentally Induced Seizures in Rats*, Epilepsia, vol. 31, Suppl. 2, (1990), pp. S7-S19.

Alvarez, et al., *Sympathetic Neural Activation in Visceral Obesity*, Circulation, Nov. 12, 2002, pp. 2533-2536.

Hammond, et al., *Vagus Nerve Stimulation in Humans: Neurophysiological Studies and Electrophysiological Monitoring*, Epilepsia, vol. 31, Suppl. 2, (1990), pp. S51-S59.

Heck, et al., *Vagus Nerve Stimulation Therapy, Epilepsy, and Device Parameters*, Neurology 59, Suppl 4, Sep. 2002, pp. S31-S37.

Terry, et al., *An Implantable Neurocybernetic Prosthesis System*, Epilepsia, vol. 31, Suppl. 2, (1990), pp. S33-S37.

Lockard, et al., *Feasibility and Safety of Vagal Stimulation in Monkey Model*, Epilepsia, vol. 31, Suppl. 2, (1990), pp. S20-S26.

Koo, et al., *Human Vagus Nerve Electrophysiology*, J Clin Neurophysiol, Sep. 2001, 18(5), pp. 429-433.

Binks, et al., *High Strength Stimulation of the Vagus Nerve in Awake Humans: A Lack of Cardiorespiratory Effects*, Respiration Physiology, vol. 127, (2001), pp. 125-133.

Andrews, Russell J., *Neuromodulation I. Techniques—Deep Brain Stimulation, Vagus Nerve Stimulation, and Transcranial Magnetic Stimulation*, Ann. N.Y. Acad. Sci. 993: 1-13 (2003).

Upton, et al., *Autonomic Stimulation*, Pace, vol. 14, Jan. 1991, pp. 50-69.

Engeland, et al., *Splanchnic Nerve Stimulation Modulates Steroid Secretion in Hypophysectomized Dogs*, Neuroendocrinology, vol. 50, (1989), pp. 124-131.

Accomero, Neri, et al., *J. Physiol.* 273: 539-560, 1977, "Selective Activation of Peripheral Nerve Fibre Groups of Different Diameter by Triangular Shaped Stimulus Pulses."

Andrews, P.L.R., et al., *J. Physiol.*, 351: 473-490, 1984, "Interactions Between Splanchnic and Vagus Nerves in the Control of Mean Intragastric Pressure in the Ferret."

Becker, M.D., James M., et al., *Surgery* vol. 89, No. 4: 466-477, 1981, "Myoelectric control of gastrointestinal and biliary motility: A review."

Blackshaw, L.A., et al., *Journal of the Autonomic Nervous System*, 66: 179-188, 1997, "Vagal and sympathetic influences on the ferret low oesophageal sphincter."

Bugbee, Martin, et al., Webpage, 1996, "Design of a Selective Nerve Stimulator."

Delbro, D., et al., *Acta Physiol Scand*, 110: 137-144, 1980, "Non-ganglionic cholinergic excitatory pathways in the sympathetic supply to the feline stomach."

Deloof, S., *Journal of the Autonomic Nervous System*, 22: 1-10, 1988, "Sympathetic control of antral and pyloric electrical activity in the rabbit."

Fang, Zi-Ping, et al., *Med. & Bio. Eng. & Comput.*,29:543-547, 1991, "Alternate excitation of large and small axons with different stimulation waveforms: an application to muscle activation."

Fukushima, K., et al., *Pflügers Arch.* 358:235-242, 1975, "Differential Blocking of Motor Fibers by Direct Current."

Hopp, F.A., et al., *The American Physiological Society*, 1980, "Effect of anodal blockade of myelinated fibers on vagal C-fiber afferents."

Ito, Shigeo, et al., *Gen. Pharmac*, vol. 24, No. 2: 291-298, 1993, "Gastric Vasodilator and Motor Responses to Splanchnic Stimulation and Tachykinins in the Dog."

Jaw, F.-S, et al., *Journal of Neuroscience Methods*, 37:169-172, 1991, "A modified "triangular pulse" stimulator for C-fibers stimulation."

Lerman, M.D., Sheldon H., et al., *Journal of Surgical Research* 32: 15-23, 1982, "Gastric Motor Response to Sympathetic Nerve Stimulation."

Lerman, M.D., Sheldon H., et al, *Surgery* vol. 89, No. 4: 460-465, 1981, "Pyloric motor response to sympathetic nerve stimulation in dogs."

Nakazato, Yoshikazu, et al., *Journal of the Autonomic Nervous System*, 20: 35-42, 1987, "Atropine- and hexamethonium-resistant motor response to greater splanchnic nerve stimulation in the dog stomach."

Nakazato, Yoshikazu, et al., *Jap. J. Pharmac*, 20: 131-141, 1970, "Gastric Motor and Inhibitor Response to Stimulation of the Sympathetic Nerve in the Dog."

Sweeney, James D., et al., IEEE Transactions on Biomedical Engineering, vol. BME-33, No. 6: 541-549, 1986, "An Asymmetric Two Electrode Cuff for Generation of Unidirectionally Propagated Action Potentials."

Thorén, Peter, et al., *J. Appl. Physiol.: Respir. Environ. Exercise Physiol.* 42: 461-465, 1977, "Anodal block of medullated cardiopulmonary vagal afferents in cats."

World J. Gastroenterol, http://wjgnet.com, 4(5): 426-429, 1988, "Modulation of hypothalamic arcuate nucleus on gastric motility in rats."

Ahren, B.; *Sympathetic Nerve Stimulation Versus Pancreatic Norepinephrine Infusion in the Dog: 1)Effects on Basal Release of Insulin and Glucagon*; Endocrinology; Mar. 1986; pp. 323-331; vol. 121, No. 1.

Alamo, L.; *Electrically-Evoked Catecholamine Release from Cat Adrenals*; Biochemical Pharmacology; Nov. 1990; pp. 973-978; vol. 42, No. 5.

Bloom, S.; *The Adrenal Contribution to the Neuroendocrine Responses to Splanchnic Nerve Stimulation in Conscious Calves*; Journal of Physiology; Jul. 1987; pp. 513-526; vol. 397.

Buckley, N.; *Circulatory Effects of Splanchnic Nerve Stimulation in Developing Swine*; American Journal of Physiology; Apr. 1984; pp. H69-H74; vol. 248.

Cigaina, V.; *Long-Term Effects of Gastric Pacing to Reduce Feed Intake in Swine*; Obesity Surgery; 1996; pp. 250-253; vol. 6.

Cummings, D.; *Plasma Ghrelin Levels after Diet-Induced Weight Loss r Gastric Bypass Surgery*; The New England Journal of Medicine; May 2002; pp. 1623-1630; vol. 346, No. 21.

Cuschieri, A.; *Blateral Endoscopic Splanchnicectomy through a Posterior Thoracoscopic Approach*; J.R. Coll. Surg. Edinb.; Feb. 1994; pp. 44-47; vol. 39.

Edwards, A.; *Adrenal Catecholamine Output in Response to Stimulation of the Splanchnic Nerve in Bursts in the Conscious Calf*; Journal of Physiology; Sep. 1981; pp. 409-419; vol. 327.

Edwards, A.; *Adrenal Medullary Responses to Stimulation of the Splanchnic Nerve in the Conscious Calf* Journal of Physiology; Jan. 1980; pp. 15-27; vol. 308.

Edwards, A.; *The Effect of Splanchnic Nerve Stimulation on Adrenocortical Activity in Conscious Calves*; Journal of Physiology; Apr. 1986; pp. 385-396; vol. 382.

Edwards, A.; *The Glycogenolytic Response to Stimulation of the Splanchnic Nerves in Adrenalectomized Calves, Sheep, Dogs, Cats, and Pigs*; Journal of Physiology; Nov. 1970; pp. 741-759; vol. 213.

Engeland, W.; *Splanchnic Nerve Stimulation Modulates Steroid Secretion in Hypophysectomized Dogs*; Neuroendocrinology; Aug. 1988; pp. 124-131; vol. 50.

Furness, J.; *Effects of Vagal and Splanchnic Section on Food Intake, Weight, Serum Leptin, and Hypothalamic Neuropeptide Y in Rat*; Autonomic Neuroscience: Basic and Clinical; Feb. 2001; pp. 28-36; vol. 92.

Kuo, D.; *A Wide Field Electron Microscope Analysis of the Fiber Constituents of the Major Splanchnic Nerve in Cat*; The Journal of Comparative Neurology; Apr. 1982; pp. 49-58; vol. 210.

Kurose, T.; *Mechanism of Sympathetic Neural Regulation of Insulin, Somatostatin, and Glucagon Secretion*; American Journal of Physiology; Mar. 1989; pp. E220-E227; vol. 258.

Naidoo, N.; *Thoracic Splanchnic Nerves: Implications for Splanchnic Denervation*; Journal of Anatomy; Jun. 2001; pp. 585-590; vol. 199.

Peterson, H.; *Body Fat and the Activity of the Autonomic Nervous System*; The New England Journal of Medicine; Apr. 1988; pp. 1078-1083; vol. 318, No. 17.

Stoddard, S.; *Adrenal Medullary Secretion with Splachnic Stimulation in Spinal Cats*; Journal of the Autonomic Nervous System; Apr. 1991; pp. 105-116; vol. 38.

Strickland, T.; *Performance of Local Anesthetic and Placebo Splanchnic Blocks via Indwelling Catheters to Predict Benefit from Thoracoscopic Splanchnicectomy in a Patient with Intractable Pancreatic Pain*; Anesthesiology; Jun. 1995; pp. 980-983; vol. 84.

Wilkinson, H.; *Percutaneous Radiofrequency Upper Thorac Sympathectomy*; Neurosurgey; Aug. 1994; pp. 715-725; vol. 38, No. 4.

Tran, M.A., et al., *J. Pharmacol* (Paris), 1985, 16, 2, 171-179, "Adrenergic Neurohumoral Influences of FFA Release From Bone Marrow Adipose Tissue."

Sato, T, et al., *National Library of Medicine*, Jul. 20, 1999; 100(3):299-304, "Novel therapeutic strategy against central baroreflex failure: a bionic baroreflex system."

* cited by examiner

PULSE GENERATOR SCHEMATIC

CATHETER-TYPE LEAD/ELECTRODE ASSEMBLY

BALANCED BIPHASE WAVE FOR

ASYMMETRIC WAVE FORM ENHANCED ANODAL BLOCK

FIGURE Y-QUADRAPOLAR BLOCKING ELECTRODE (Weight of single animal from each of Cohort 1 and Cohort 2 where the stimulator was turned off divided by the average weight of the three Control animals.)

SPLANCHNIC NERVE STIMULATION FOR TREATMENT OF OBESITY

CROSS REFERENCE TO RELATED APPLICATIONS

This is a continuation-in-part application of U.S. patent application. Ser. No. 10/272,430, filed Oct. 16, 2002, now U.S. Pat. No. 7,236,822, and entitled "Wireless Electric Modulation of Sympathetic Nervous System," which is a continuation-in-part application of U.S. patent application. Ser. No. 10/243,612, filed Sep. 13, 2002, now U.S. Pat. No. 7,239,912, and entitled "Electric Modulation of Sympathetic Nervous System." Each of these two earlier-filed priority applications claim the priority benefit of five U.S. provisional patent applications: U.S. Provisional Patent Application No. 60/366,750, filed Mar. 22, 2002; U.S. Provisional Patent Application No. 60/370,311, filed Apr. 5, 2002; U.S. Provisional Patent Application No. 60/379,605, filed May 10, 2002; U.S. Provisional Patent Application No. 60/384,219, filed May 30, 2002; and U.S. Provisional Patent Application No. 60/386,699, filed Jun. 10, 2002.

Furthermore, the instant application claims the priority benefit of six other U.S. provisional patent applications: U.S. Provisional Patent Application No. 60/450,534, filed Feb. 25, 2003; U.S. Provisional Patent Application No. 60/452,361, filed Mar. 5, 2003; U.S. Provisional Patent Application No. 60/466,890, filed Apr. 30, 2003; U.S. Provisional Patent Application No. 60/466,805, filed Apr. 30, 2003; U.S. Provisional Patent Application No. 60/479,933, filed Jun. 19, 2003; and U.S. Provisional Patent Application No. 60/496,437, filed Aug. 20, 2003.

The entireties of all of these priority applications are hereby incorporated by reference.

BACKGROUND OF THE INVENTION

1. Field of the Invention

The invention relates to nerve stimulation for the treatment of medical conditions.

2. Description of the Related Art

Obesity is an epidemic in the U.S. with a prevalence of about 20 percent. Annual U.S. healthcare costs associated with obesity are estimated to exceed $200 billion dollars. Obesity is defined as a body mass index (BMI) that exceeds 30 kg/m$^2$. Normal BMI is 18.5-25 kg/m$^2$, and overweight persons have BMIs of 25-30. Obesity is classified into three groups: moderate (Class 1), severe (Class II), and very severe (Class III). Patients with BMIs that exceed 30 are at risk for significant comorbidities such as diabetes, heart and kidney disease, dyslipidemia, hypertension, sleep apnea, and orthopedic problems.

Obesity results from an imbalance between food intake and energy expenditure such that there is a net increase in fat reserves. Excessive food intake, reduced energy expenditure, or both may cause this imbalance. Appetite and satiety, which control food intake, are partly controlled in the brain by the hypothalamus. Energy expenditure is also partly controlled by the hypothalamus. The hypothalamus regulates the autonomic nervous system of which there are two branches, the sympathetic and the parasympathetic. The sympathetic nervous system generally prepares the body for action by increasing heart rate, blood pressure, and metabolism. The parasympathetic system prepares the body for rest by lowering heart rate, lowering blood pressure, and stimulating digestion. Destruction of the lateral hypothalamus results in hunger suppression, reduced food intake, weight loss, and increased sympathetic activity. In contrast, destruction of the ventromedial nucleus of the hypothalamus results in suppression of satiety, excessive food intake, weight gain, and decreased sympathetic activity. The splanchnic nerves carry sympathetic neurons that supply, or innervate, the organs of digestion and adrenal glands, and the vagus nerve carries parasympathetic neurons that innervate the digestive system and are involved in the feeding and weight gain response to hypothalamic destruction.

Experimental and observational evidence suggests that there is a reciprocal relationship between food intake and sympathetic nervous system activity. Increased sympathetic activity reduces food intake and reduced sympathetic activity increases food intake. Certain peptides (e.g. neuropeptide Y, galanin) are known to increase food intake while decreasing sympathetic activity. Others such as cholecystokinin, leptin, enterostatin, reduce food intake and increase sympathetic activity. In addition, drugs such as nicotine, ephedrine, caffeine, subitramine, dexfenfluramine, increase sympathetic activity and reduce food intake.

Ghrelin is another peptide that is secreted by the stomach that is associated with hunger. Peak plasma levels occur just prior to mealtime, and ghrelin levels are increased after weight loss. Sympathetic activity can suppress ghrelin secretion. PYY is a hormone released from the intestine that plays a role in satiety. PYY levels increase after meal ingestion. Sympathetic activity can increase PYY plasma levels.

Appetite is stimulated by various psychosocial factors, but is also stimulated by low blood glucose levels. Cells in the hypothalamus that are sensitive to glucose levels are thought to play a role in hunger stimulation. Sympathetic activity increases plasma glucose levels. Satiety is promoted by distention of the stomach and delayed gastric emptying. Sympathetic activity reduces gastric and duodenal motility, causes gastric distention, and can increase pyloric sphincter, which can result in distention and delayed gastric emptying.

The sympathetic nervous system plays a role in energy expenditure and obesity. Genetically inherited obesity in rodents is characterized by decreased sympathetic activity to adipose tissue and other peripheral organs. Catecholamines and cortisol, which are released by the sympathetic nervous system, cause a dose-dependent increase in resting energy expenditure. In humans, there is a reported negative correlation between body fat and plasma catecholamine levels. Overfeeding or underfeeding lean human subjects has a significant effect on energy expenditure and sympathetic nervous system activation. For example, weight loss in obese subjects is associated with a compensatory decrease in energy expenditure, which promotes the regain of previously lost weight. Drugs that activate the sympathetic nervous system, such as ephedrine, caffeine and nicotine, are known to increase energy expenditure. Smokers are known to have lower body fat stores and increased energy expenditure.

The sympathetic nervous system also plays an important role in regulating energy substrates for increased expenditure, such as fat and carbohydrate. Glycogen and fat metabolism are increased by sympathetic activation and are needed to support increased energy expenditure.

Animal research involving acute electrical activation of the splanchnic nerves under general anesthesia causes a variety of physiologic changes. Electrical activation of a single splanchnic nerve in dogs and cows causes a frequency dependent increase in catecholamine, dopamine, and cortisol secretion. Plasma levels can be achieved that cause increased energy expenditure. In adrenalectomized anesthetized pigs, cows, and dogs, acute single splanchnic nerve activation causes increased blood glucose and reduction in glycogen liver stores. In dogs, single splanchnic nerve electrical activation causes increased pyloric sphincter tone and decrease duodenal motility. Sympathetic and splanchnic nerve activation can cause suppression of insulin and leptin hormone secretion.

First line therapy for obesity is behavior modification involving reduced food intake and increased exercise. However, these measures often fail and behavioral treatment is supplemented with pharmacologic treatment using the pharmacologic agents noted above to reduce appetite and increase energy expenditure. Other pharmacologic agents that can cause these affects include dopamine and dopamine analogs, acetylcholine and cholinesterase inhibitors. Pharmacologic therapy is typically delivered orally and results in systemic side effects such as tachycardia, sweating, and hypertension. In addition, tolerance can develop such that the response to the drug reduces even at higher doses.

More radical forms of therapy involve surgery. In general, these procedures reduce the size of the stomach and/or reroute the intestinal system to avoid the stomach. Representative procedures are gastric bypass surgery and gastric banding. These procedures can be very effective in treating obesity, but they are highly invasive, require significant lifestyle changes, and can have severe complications.

Experimental forms of treatment for obesity involve electrical stimulation of the stomach (gastric pacing) and the vagus nerve (parasympathetic system). These therapies use a pulse generator to stimulate electrically the stomach or vagus nerve via implanted electrodes. The intent of these therapies is to reduce food intake through the promotion of satiety and or reduction of appetite, and neither of these therapies is believed to affect energy expenditure. U.S. Pat. No. 5,423,872 to Cigaina describes a putative method for treating eating disorders by electrically pacing the stomach. U.S. Pat. No. 5,263,480 to Wernicke discloses a putative method for treating obesity by electrically activating the vagus nerve. Neither of these therapies increases energy expenditure.

SUMMARY OF THE INVENTION

The invention includes a method for treating obesity or other disorders by electrically activating the sympathetic nervous system with a wireless electrode inductively coupled with a radiofrequency field. Obesity can be treated by activating the efferent sympathetic nervous system, thereby increasing energy expenditure and reducing food intake. Stimulation is accomplished using a radiofrequency pulse generator and electrodes implanted near, or attached to, various areas of the sympathetic nervous system, such as the sympathetic chain ganglia, the splanchnic nerves (greater, lesser, least), or the peripheral ganglia (e.g., celiac, mesenteric). Preferably, the obesity therapy will employ electrical activation of the sympathetic nervous system that innervates the digestive system, adrenals, and abdominal adipose tissue, such as the splanchnic nerves or celiac ganglia. Afferent stimulation can also be accomplished to provide central nervous system satiety. Afferent stimulation can occur by a reflex arc secondary to efferent stimulation. Preferably, both afferent and efferent stimulation can be achieved.

This method of obesity treatment may reduce food intake by a variety of mechanisms, including, for example, general increased sympathetic system activation and increasing plasma glucose levels upon activation. Satiety may be produced through direct effects on the pylorus and duodenum that cause reduced peristalsis, stomach distention, and/or delayed stomach emptying. In addition, reducing ghrelin secretion and/or increasing PYY secretion may reduce food intake. The method can also cause weight loss by reducing food absorption, presumably through a reduction in secretion of digestive enzymes and fluids and changes in gastrointestinal motility. We have noted an increased stool output, increased PYY concentrations (relative to food intake), and decreased ghrelin concentrations (relative to food intake) as a result of splanchnic nerve stimulation according to the stimulation parameters disclosed herein.

This method of obesity treatment may also increase energy expenditure by causing catecholamine, cortisol, and dopamine release from the adrenal glands. The therapy can be titrated to the release of these hormones. Fat and carbohydrate metabolism, which are also increased by sympathetic nerve activation, will accompany the increased energy expenditure. Other hormonal effects induced by this therapy may include reduced insulin secretion. Alternatively, this method may be used to normalize catecholamine levels, which are reduced with weight gain.

Electrical sympathetic activation for treating obesity is preferably accomplished without causing a rise in mean arterial blood pressure (MAP). This can be achieved by using an appropriate stimulation pattern with a relatively short signal-on time (or "on period") followed by an equal or longer signal-off time (or "off period"). During activation therapy, a sinusoidal-like fluctuation in the MAP can occur with an average MAP that is within safe limits. Alternatively, an alpha sympathetic receptor blocker, such as prazosin, can be used to blunt the increase in MAP.

Electrical sympathetic activation can be titrated to the plasma level of catecholamines achieved during therapy. This would allow the therapy to be monitored and safe levels of increased energy expenditure to be achieved. The therapy can also be titrated to plasma ghrelin levels or PYY levels.

Electrical modulation (inhibition or activation) of the sympathetic nerves can also be used to treat other eating disorders such as anorexia or bulimia. For example, inhibition of the sympathetic nerves can be useful in treating anorexia. Electrical modulation of the sympathetic nerves may also be used to treat gastrointestinal diseases such as peptic ulcers, esophageal reflux, gastroparesis, and irritable bowel. For example, stimulation of the splanchnic nerves that innervate the large intestine may reduce the symptoms of irritable bowel syndrome, characterized by diarrhea. Pain may also be treated by electric nerve modulation of the sympathetic nervous system, as certain pain neurons are carried in the sympathetic nerves. This therapy may also be used to treat type II diabetes. These conditions can require varying degrees of inhibition or stimulation.

Some embodiments include a method for treating a medical condition, the method comprising electrically activating a splanchnic nerve in a mammal according to a stimulation pattern configured to result in net weight loss in the mammal; wherein the stimulation pattern comprises a stimulation intensity, an on time, and an off time; and wherein the stimulation pattern is configured such that the ratio of the on time to the off time is about 0.75 or less.

In some embodiments the stimulation pattern is configured such that the ratio of the on time to the off time is about 0.5 or less, and in some embodiments, about 0.3 or less.

In some embodiments the stimulation pattern is configured such that the on time is about two minutes or less. In some embodiments the stimulation pattern is configured such that the on time is about one minute or less. In some embodiments the stimulation pattern is configured such that the on time is about one minute or less and the off time is about one minute or more.

In some embodiments the stimulation pattern is configured such that the on time is greater than about 15 seconds. In some embodiments the stimulation pattern is configured such that the on time is greater than about 30 seconds.

Some embodiments further comprise varying the stimulation intensity over time, such as by increasing the stimulation intensity over time, sometimes daily.

Some embodiments further comprise creating a unidirectional action potential in the splanchnic nerve. This can involve creating an anodal block in the splanchnic nerve.

Some embodiments include a method for treating a medical condition, the method comprising electrically activating a splanchnic nerve in a mammal according to a stimulation pattern for a first time period; wherein the stimulation pattern comprises a stimulation intensity and is configured to result in net weight loss in the mammal during the first time period; and reducing or ceasing the electrical activation of the splanchnic nerve for a second time period, such that the mammal loses net weight during the second time period.

In some embodiments the first time period is between about 2 weeks and about 15 weeks. In some embodiments the first time period is between about 6 weeks and about 12 weeks. In some embodiments the second time period is between about 1 week and about 6 weeks. In some embodiments the second time period is between about 2 weeks and about 4 weeks.

In some embodiments the electrically activating the splanchnic nerve comprises delivering a stimulation intensity to the splanchnic nerve that is approximately equal to the stimulation intensity required to produce skeletal muscle twitching in the mammal. In some embodiments the stimulation intensity to the splanchnic nerve is at least about two times the stimulation intensity required to produce skeletal muscle twitching in the mammal. In some embodiments the stimulation intensity to the splanchnic nerve is at least about five times the stimulation intensity required to produce skeletal muscle twitching in the mammal. In some embodiments the stimulation intensity to the splanchnic nerve is at least about eight times the stimulation intensity required to produce skeletal muscle twitching in the mammal.

Some embodiments include a method for treating a medical condition, the method comprising electrically activating a splanchnic nerve in a mammal according to a stimulation pattern for a first time period within a period of about 24 hours, said stimulation pattern comprising a stimulation intensity and being configured to result in net weight loss in the mammal; and ceasing the electrical activation of the a splanchnic nerve for a second time period within the period of about 24 hours.

Some embodiments further comprise repeating the steps of electrically activating and ceasing the electrical activation. In some embodiments the first time period plus the second time period equals about 24 hours.

Some embodiments include a method for treating a medical condition, the method comprising electrically activating a splanchnic nerve in a mammal according to a stimulation pattern configured to result in net weight loss in the mammal; wherein the stimulation pattern comprises a stimulation intensity and a frequency; and wherein the frequency is about 15 Hz or greater, to minimize skeletal muscle twitching.

In some embodiments the frequency is about 20 Hz or greater. In some embodiments the frequency is about 30 Hz or greater.

In some embodiments the stimulation intensity is at least about 5 times the stimulation intensity required to produce skeletal muscle twitching in the mammal. In some embodiments the stimulation intensity is at least about 10 times the stimulation intensity required to produce skeletal muscle twitching in the mammal, and the frequency is about 20 Hz or greater.

Some embodiments include a method for producing weight loss, the method comprising electrically activating a splanchnic nerve in a mammal according to a stimulation pattern comprising a stimulation intensity and a frequency; and the stimulation pattern is configured to decrease absorption of food from the gastrointestinal tract, resulting in increased stool output in the mammal.

In some embodiments the frequency is about 15 Hz or greater, about 20 Hz or greater, and/or about 30 Hz or greater.

In some embodiments the stimulation intensity is at least about 5 times the stimulation intensity required to produce skeletal muscle twitching in the mammal.

In some embodiments the stimulation intensity is at least about 10 times the stimulation intensity required to produce skeletal muscle twitching in the mammal, and the frequency is about 20 Hz or greater.

Some embodiments include a method for treating a medical condition, the method comprising placing an electrode in proximity to a splanchnic nerve in a mammal above the diaphragm; and electrically activating the splanchnic nerve.

Some embodiments further comprise placing the electrode in contact with the splanchnic nerve. In some embodiments the electrode is helical or has a cuff, and further comprising attaching the electrode to the splanchnic nerve.

In some embodiments the placing is transcutaneous (that is, percutaneous). In some embodiments the placing is into a blood vessel of the mammal. In some embodiments the blood vessel is an azygous vein.

Some embodiments further comprise electrically activating the electrode and observing the patient for skeletal muscle twitching to assess placement of the electrode near the splanchnic nerve.

Some embodiments include a method for treating a medical condition, the method comprising placing an electrode into a blood vessel of a mammal, in proximity to a splanchnic nerve of the mammal; and electrically activating the splanchnic nerve via the electrode. In some embodiments the blood vessel is an azygous vein. In some embodiments the electrically activating is according to a stimulation-pattern configured to result in net weight loss in the mammal.

Some embodiments include a method for treating a medical condition, the method comprising electrically activating a splanchnic nerve in a mammal according to a stimulation pattern configured to result in net weight loss in the mammal; wherein the stimulation pattern comprises an on time; and wherein the on time is adjusted based on a blood pressure of the mammal.

Some embodiments include a method for treating a medical condition, the method comprising electrically activating a splanchnic nerve in a mammal according to a stimulation pattern configured to result in net weight loss in the mammal; wherein the stimulation pattern comprises an on time; and wherein the on time is adjusted based on a plasma PYY concentration and/or a plasma ghrelin concentration in the mammal.

Some embodiments include a method for treating a medical condition, the method comprising electrically activating a splanchnic nerve in a mammal according to a stimulation pattern, wherein the stimulation pattern comprises a current amplitude; wherein the current amplitude is adjusted based on skeletal muscle twitching in the mammal.

Some embodiments include a method for treating a medical condition, the method comprising electrically activating a splanchnic nerve in a mammal according to a stimulation pattern, wherein the stimulation pattern comprises a current amplitude and a pulse width; wherein the current amplitude is increased to a first level at which skeletal muscle twitching begins to occur in the mammal; keeping the current amplitude at or near the first level until the skeletal muscle twitching decreases or ceases.

Some embodiments further comprise further increasing the current amplitude as habituation to the skeletal muscle twitching occurs. Some embodiments further comprise further increasing the current amplitude to a second level at which skeletal muscle twitching begins to recur, the second level being greater than the first level.

Some embodiments include a method for treating a medical condition, the method comprising electrically activating a splanchnic nerve in a mammal according to a stimulation pattern, wherein the stimulation pattern comprises a current amplitude and a pulse width; wherein the current amplitude is increased to a first level at which skeletal muscle twitching begins to occur in the mammal; increasing the pulse width while keeping the current amplitude at about the first level or below the first level.

Some embodiments include a method for treating a medical condition, the method comprising electrically activating a splanchnic nerve in a mammal according to a stimulation pattern, wherein the stimulation pattern comprises a current amplitude; wherein the current amplitude is increased to a first level at which skeletal muscle twitching begins to occur in the mammal; and sensing the muscle twitching with a sensor in electrical communication with the electrode.

In some embodiments the sensor is electrical. In some embodiments the sensor is mechanical.

Some embodiments further comprise further increasing the current amplitude as habituation to the skeletal muscle twitching implanting the sensor near the abdominal wall to sense abdominal muscle twitching.

Some embodiments include a device for treating a medical condition, the device comprising an electrode configured to stimulate electrically a splanchnic nerve in a mammal; a generator configured to deliver an electrical signal to the electrode; and a sensor in electrical communication with the generator, the sensor configured to sense muscle twitching; wherein the device is programmed to stimulate electrically the splanchnic nerve according to a stimulation pattern, wherein the stimulation pattern comprises a current amplitude and a pulse width; wherein the device is further programmed to increase the current amplitude to a first level at which skeletal muscle twitching begins to occur, and temporarily hold the current amplitude at or near the first level until the skeletal muscle twitching decreases or ceases.

In some embodiments the device is further programmed to increase the pulse width while keeping the current amplitude at or near the first level. In some embodiments the device is further programmed to increase the current amplitude as habituation to the muscle twitching occurs. In some embodiments the device is further programmed to increase the current amplitude to a second level at which skeletal muscle twitching begins to recur, the second level being greater than the first level.

In some embodiments the device is compatible with magnetic resonance imaging. In some embodiments the device comprises a nanomagnetic material.

Some embodiments include a method for treating a medical condition, the method comprising electrically activating a splanchnic nerve in a mammal according to a stimulation pattern that is configured to result in net weight loss in the mammal without causing a substantial rise in a blood pressure of the mammal.

Some embodiments include a method for treating a medical condition, the method comprising electrically activating a splanchnic nerve in a mammal according to a stimulation pattern that is configured to result in net weight loss in the mammal without causing prolonged skeletal muscle twitching in the mammal. Avoiding prolonged skeletal muscle twitching, in this context, refers to the fact that as soon as the stimulation threshold for muscle twitching is reached in this method (as the stimulation intensity is increased), current amplitude (or an analogous parameter, such as voltage) is held at or below this level until habituation to muscle twitching is reached by the animal. At that point, the current amplitude can then be increased until muscle twitching recurs at a higher stimulation intensity. Then the process is repeated, as a "ramp up" protocol, while minimizing skeletal muscle twitching.

The invention will be best understood from the attached drawings and the following description, in which similar reference characters refer to similar parts.

DETAILED DESCRIPTION OF EXEMPLARY EMBODIMENTS

The human nervous system is a complex network of nerve cells, or neurons, found centrally in the brain and spinal cord and peripherally in the various nerves of the body. Neurons have a cell body, dendrites and an axon. A nerve is a group of neurons that serve a particular part of the body. Nerves can contain several hundred neurons to several hundred thousand neurons. Nerves often contain both afferent and efferent neurons. Afferent neurons carry signals back to the central nervous system and efferent neurons carry signals to the periphery. A group of neuronal cell bodies in one location is known as a ganglion. Electrical signals are conducted via neurons and nerves. Neurons release neurotransmitters at synapses (connections) with other nerves to allow continuation and modulation of the electrical signal. In the periphery, synaptic transmission often occurs at ganglia.

The electrical signal of a neuron is known as an action potential. Action potentials are initiated when a voltage potential across the cell membrane exceeds a certain threshold. This action potential is then propagated down the length of the neuron. The action potential of a nerve is complex and represents the sum of action potentials of the individual neurons in it.

Neurons can be myelinated and unmyelinated, of large axonal diameter and small axonal diameter. In general, the speed of action potential conduction increases with myelination and with neuron axonal diameter. Accordingly, neurons are classified into type A, B and C neurons based on myelination, axon diameter, and axon conduction velocity. In terms of axon diameter and conduction velocity, A is greater than B which is greater than C.

Figure 1:
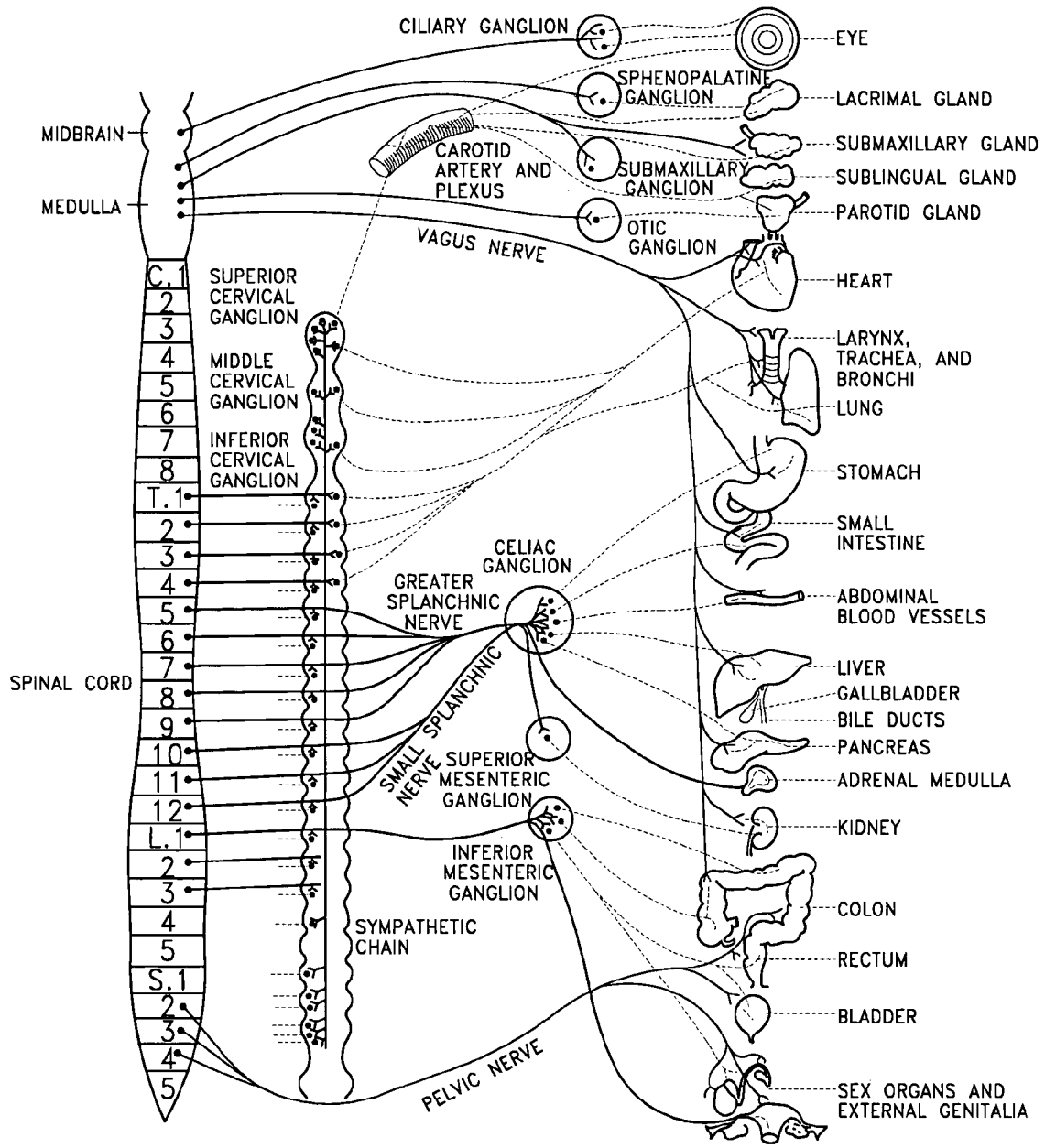
FIG. 1 is a diagram of the efferent autonomic nervous system.

The autonomic nervous system is a subsystem of the human nervous system that controls involuntary actions of the smooth muscles (blood vessels and digestive system), the heart, and glands, as shown in FIG. 1. The autonomic nervous system is divided into the sympathetic and parasympathetic systems. The sympathetic nervous system generally prepares the body for action by increasing heart rate, increasing blood pressure, and increasing metabolism. The parasympathetic system prepares the body for rest by lowering heart rate, lowering blood pressure, and stimulating digestion.

Figure 2:
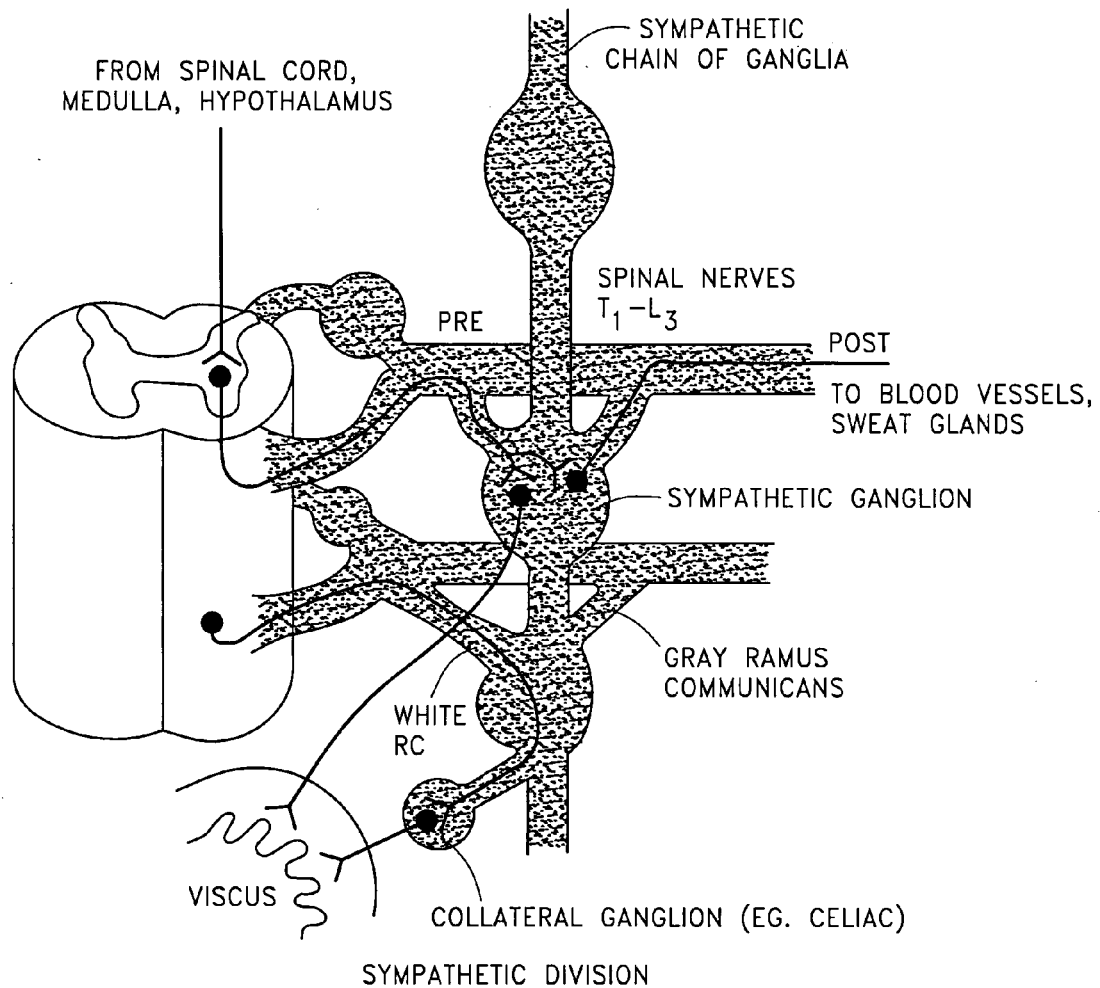
FIG. 2 is a diagram of sympathetic nervous system anatomy.

The hypothalamus controls the sympathetic nervous system via descending neurons in the ventral horn of the spinal cord, as shown in FIG. 2. These neurons synapse with preganglionic sympathetic neurons that exit the spinal cord and form the white communicating ramus. The preganglionic neuron will either synapse in the paraspinous ganglia chain or pass through these ganglia and synapse in a peripheral, or collateral, ganglion such as the celiac or mesenteric. After synapsing in a particular ganglion, a postsynaptic neuron continues on to innervate the organs of the body (heart, intestines, liver, pancreas, etc.) or to innervate the adipose tissue and glands of the periphery and skin. Preganglionic neurons of the sympathetic system can be both small-diameter unmyelinated fibers (type C-like) and small-diameter myelinated fibers (type B-like). Postganglionic neurons are typically unmyelinated type C neurons.

Figure 3:
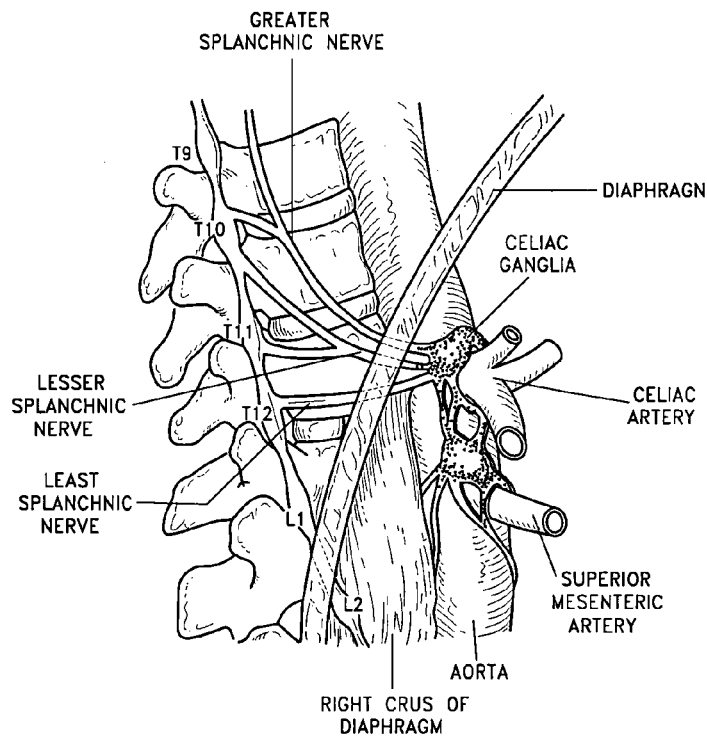
FIG. 3 is an elevation view of the splanchnic nerves and celiac ganglia.

Several large sympathetic nerves and ganglia are formed by the neurons of the sympathetic nervous system as shown in FIG. 3. The greater splanchnic nerve (GSN) is formed by efferent sympathetic neurons exiting the spinal cord from thoracic vertebral segment numbers 4 or 5 (T4 or T5) through thoracic vertebral segment numbers 9 or 10 or 11 (T9, T10, or T11). The lesser splanchnic (lesser SN) nerve is formed by preganglionic fibers sympathetic efferent fibers from T10 to T12 and the least splanchnic nerve (least SN) is formed by fibers from T12. The GSN is typically present bilaterally in animals, including humans, with the other splanchnic nerves having a more variable pattern, present unilaterally or bilaterally and sometimes being absent. The splanchnic nerves run along the anterior-lateral aspect of the vertebral bodies and pass out of the thorax and enter the abdomen through the crus of the diaphragm. The nerves run in proximity to the azygous veins. Once in the abdomen, neurons of the GSN synapse with postganglionic neurons primarily in celiac ganglia. Some neurons of the GSN pass through the celiac ganglia and synapse on in the adrenal medulla. Neurons of the lesser SN and least SN synapse with post-ganglionic neurons in the mesenteric ganglia.

Postganglionic neurons, arising from the celiac ganglia that synapse with the GSN, innervate primarily the upper digestive system, including the stomach, pylorus, duodenum, pancreas, and liver. In addition, blood vessels and adipose tissue of the abdomen are innervated by neurons arising from the celiac ganglia/greater splanchnic nerve. Postganglionic neurons of the mesenteric ganglia, supplied by preganglionic neurons of the lesser and least splanchnic nerve, innervate primarily the lower intestine, colon, rectum, kidneys, bladder, and sexual organs, and the blood vessels that supply these organs and tissues.

In the treatment of obesity, a preferred embodiment involves electrical activation of the greater splanchnic nerve of the sympathetic nervous system. Preferably unilateral activation would be utilized, although bilateral activation can also be utilized. The celiac ganglia can also be activated, as well as the sympathetic chain or ventral spinal roots.

Electrical nerve modulation (nerve activation or inhibition) is accomplished by applying an energy signal (pulse) at a certain frequency to the neurons of a nerve (nerve stimulation). The energy pulse causes depolarization of neurons within the nerve above the activation threshold resulting in an action potential. The energy applied is a function of the current (or voltage) amplitude and pulse width or duration. Activation or inhibition can be a function of the frequency, with low frequencies on the order of 1 to 50 Hz resulting in activation and high frequencies greater than 100 Hz resulting in inhibition. Inhibition can also be accomplished by continuous energy delivery resulting in sustained depolarization. Different neuronal types may respond to different frequencies and energies with activation or inhibition.

Each neuronal type (i.e., type A, B, or C neurons) has a characteristic pulse amplitude-duration profile (energy pulse signal or stimulation intensity) that leads to activation. The stimulation intensity can be described as the product of the current amplitude and the pulse width. Myelinated neurons (types A and B) can be stimulated with relatively low current amplitudes, on the order of 0.1 to 5.0 milliamperes, and short pulse widths, on the order of 50 to 200 microseconds. Unmyelinated type C fibers typically require longer pulse widths on the order of 300 to 1,000 microseconds and higher current amplitudes. Thus, in one embodiment, the stimulation intensity for efferent activation would be in the range of about 0.005-5.0 mAmp-mSec).

The greater splanchnic nerve also contains type A fibers. These fibers can be afferent and sense the position or state (contracted versus relaxed) of the stomach or duodenum. Stimulation of A fibers may produce a sensation of satiety by transmitting signals to the hypothalamus. They can also participate in a reflex arc that affects the state of the stomach. Activation of both A and B fibers can be accomplished because stimulation parameters that activate efferent B fibers will also activate afferent A fibers. Activation of type C fibers may cause both afferent an efferent effects, and may cause changes in appetite and satiety via central or peripheral nervous system mechanisms.

Figure 4:
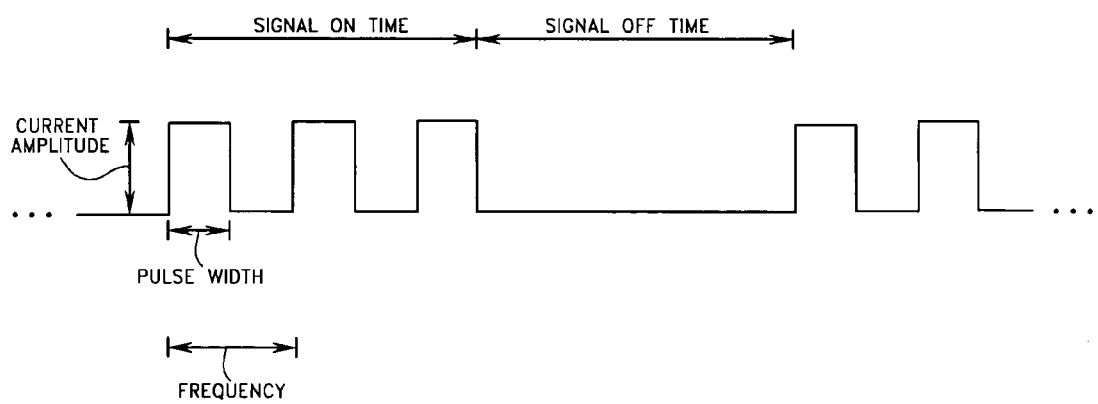
FIG. 4 is a schematic of an exemplary stimulation pattern.

Various stimulation patterns, ranging from continuous to intermittent, can be utilized. With intermittent stimulation, energy is delivered for a period of time at a certain frequency during the signal-on time as shown in FIG. 4. The signal-on time is followed by a period of time with no energy delivery, referred to as signal-off time. The ratio of the on time to the on time plus the off time is referred to as the duty cycle and it can in some embodiments range from about 1% to about 100%. Peripheral nerve stimulation is commonly conducted at nearly a continuous, or 100%, duty cycle. However, an optimal duty cycle for splanchnic nerve stimulation to treat obesity may be less than 75% in some embodiments, lees than 50% in some embodiments, or even less than 30% in further embodiments. This may reduce problems associated with muscle twitching as well as reduce the chance for blood pressure or heart rate elevations. The on time may also be important for splanchnic nerve stimulation in the treatment of obesity. Because some of the desired effects involve the release of hormones, on times sufficiently long enough to allow plasma levels to rise are important. Also gastrointestinal effects on motility and digestive secretions take time to reach a maximal effect. Thus, an on time of approximately 15 seconds, and sometimes greater than 30 seconds, may be optimal.

Superimposed on the duty cycle and signal parameters (frequency, on-time, mAmp, and pulse width) are treatment parameters. Therapy may be delivered at different intervals during the day or week, or continuously. Continuous treatment may prevent binge eating during the off therapy time. Intermittent treatment may prevent the development of tolerance to the therapy. Optimal intermittent therapy may be, for example, 18 hours on and 6 hours off, 12 hours on and 12 hours off, 3 days on and 1 day off, 3 weeks on and one week off or a another combination of daily or weekly cycling. Alternatively, treatment can be delivered at a higher interval rate, say, about every three hours, for shorter durations, such as about 2-30 minutes. The treatment duration and frequency can be tailored to achieve the desired result. The treatment duration can last for as little as a few minutes to as long as several hours. Also, splanchnic nerve activation to treat obesity can be delivered at daily intervals, coinciding with meal times. Treatment duration during mealtime may, in some embodiments, last from 1-3 hours and start just prior to the meal or as much as an hour before.

Efferent modulation of the GSN can be used to control gastric distention/contraction and peristalsis. Gastric distention or relaxation and reduced peristalsis can produce satiety or reduced appetite for the treatment of obesity. These effects can be caused by activating efferent B or C fibers at moderate to high intensities (1.0-5.0 milliAmp current amplitude and 0.150-1.0 milliseconds pulse width) and higher frequencies (10-20 Hz). Gastric distention can also be produced via a reflex arc involving the afferent A fibers. Activation of A fibers may cause a central nervous system mediated reduction in appetite or early satiety. These fibers can be activated at the lower range of stimulation intensity (0.05-0.150 mSec pulse width and 0.1-1.0 mAmp current amplitude) and higher range of frequencies given above. Contraction of the stomach can also reduce appetite or cause satiety. Contraction can be caused by activation of C fibers in the GSN. Activation of C fibers may also play a role in centrally mediated effects. Activation of these fibers is accomplished at higher stimulation intensities (5-10× those of B and A fibers) and lower frequencies (</=10 Hz).

Electrical activation of the splanchnic nerve can also cause muscle twitching of the abdominal and intercostal muscles. Stimulation at higher frequencies (>15 Hz) reduces the muscle activity, and muscle twitching is least evident or completely habituates at higher frequencies (20-30 Hz). During stimulation at 20 or 30 Hz, a short contraction of the muscles is observed followed by relaxation, such that there is no additional muscle contraction for the remainder of the stimulation. This can be due to inhibitory neurons that are activated with temporal summation.

The muscle-twitching phenomenon can also be used to help guide the stimulation intensity used for the therapy. Once the threshold of muscle twitching is reached, activation of at least the A fibers has occurred. Increasing the current amplitude beyond the threshold increases the severity of the muscle contraction and can increase discomfort. Delivering the therapy at about the threshold for muscle twitching, and not substantially higher, helps ensure that the comfort of the patient is maintained, particularly at higher frequencies. Once this threshold is reached the pulse width can be increased 1.5 to 2.5 times longer, thereby increasing the total charge delivered to the nerve, without significantly increasing the severity of the muscle twitching. By increasing the pulse width at the current, activation of B-fibers is better ensured. Hence, with an electrode placed in close contact with the nerve, a pulse width between 0.100 and 0.150 msec and a frequency of 1 Hz, the current amplitude can be increased until the threshold of twitching is observed (activation of A fibers). This will likely occur between 0.25 and 2.5 mAmps of current, depending on how close the electrode is to the nerve. It should be noted that patient comfort can be achieved at current amplitudes slightly higher than the muscle twitch threshold, or that effective therapy can be delivered at current amplitudes slightly below the muscle twitch threshold, particularly at longer pulse widths.

Habituation to the muscle twitching also occurs, such that the muscle twitching disappears after a certain time period. This allows the stimulation intensity to be increased to as much as 10× or greater the threshold of muscle twitching. This can be done without causing discomfort and ensures activation of the C fibers. It was previously thought that high stimulation intensities would result in the perception of pain, but this does not appear to be seen in experimental settings. The stimulation intensity of the muscle twitch threshold can also be used to guide therapy in this instance, because the twitch threshold may vary from patient to patient depending on the nerve and contact of the electrode with the nerve. Once the threshold of muscle twitching is determined the stimulation intensity (current×pulse width) can be increased to 5× or greater than 10× the threshold. Habituation occurs by stimulating at the threshold for up to 24 hours.

Increasing the stimulation intensity after habituation at one level occurs can bring back the muscle activity and require another period of habituation at the new level. Thus, the stimulation intensity can be increased in a stepwise manner, allowing habituation to occur at each step until the desired intensity is achieved at 5-10× the original threshold. This is important if intermittent treatment frequency is used, as the habituation process up to the desired stimulation intensity would have to occur after each interval when the device is off. Preferably, the device is programmed to allow a prolonged ramp up of intensity over several hours to days, allowing habituation to occur at each level. This is not the same as the rapid rise in current amplitude that occurs at the beginning of each on time during stimulation. This may be built or programmed directly into the pulse generator or controlled/programmed by the physician, who can take into account patient variability of habituation time.

Alternatively, the device can sense muscle twitching. One way to do this is to implant the implantable pulse generator (IPG) over the muscles that are activated. The IPG can then electrically or mechanically sense the twitching and increase the stimulation intensity as habituation occurs.

Efferent electrical activation of the splanchnic nerve can cause an increase in blood pressure, for example, the mean arterial blood pressure (MAP), above a baseline value. A drop in MAP below the baseline can follow this increase. Because a sustained increase in MAP is undesirable, the stimulation pattern can be designed to prevent an increase in MAP. One strategy would be to have a relatively short signal-on time followed by a signal-off time of an equal or longer period. This would allow the MAP to drop back to or below the baseline. The subsequent signal-on time would then raise the MAP, but it can start from a lower baseline. In this manner a sinusoidal-like profile of the MAP can be set up during therapy delivery that would keep the average MAP within safe limits.

During stimulation the MAP may rise at a rate of 0.1-1.0 mmHg/sec depending on frequency, with higher frequencies causing a more rapid rise. An acceptable transient rise in MAP would be about 10-20% of a patient's baseline. Assuming a normal MAP of 90 mmHg, a rise of 9-18 mm Hg over baseline would be acceptable during stimulation. Thus a stimulation on time of approximately 9-54 seconds is acceptable. The off time would be greater than the on time or greater than approximately 60 seconds. Habituation may also occur with the blood pressure changes. This may allow the on time to be increased beyond 60 seconds, after habituation has occurred.

In one embodiment a strategy for treating obesity using splanchnic nerve stimulation is to stimulate A fibers. The pulse width can be set to 0.05-0.15 mSec and the current can be increased (0.1-0.75 mAmp) until the threshold of muscle twitching is reached. Other parameters include a frequency of 20-30 Hz and an on time of less than 60 seconds with a duty cycle of 20-50%. Once habituation to the rise in MAP occurred the on time can be increased to greater than 60 seconds.

In another embodiment, a strategy for treating obesity by electrical activation of the splanchnic nerve involves stimulating the B and A fibers. This strategy involves stimulating the nerve at intensities 2-3× the muscle twitch threshold prior to any habituation. The pulse width can preferably be set to a range of about 0.150 mSec to 0.250 mSec with the pulse current increased (allowing appropriate habituation to occur) to achieve the desired level above the original muscle twitch threshold. Representative parameters can be the following:

Current amplitude 0.75-2.0 m Amps,
Pulse width 0.150-0.250 m Seconds,
Frequency 10-20 Hz,
On-time<60 seconds,
Off-time>60 seconds.

These parameters result in gastric relaxation and reduced peristalsis causing early satiety and activation of distention receptors in the stomach that would send satiety signals back to the central nervous system in a reflex manner. Because the effect of gastric relaxation is sustained beyond the stimulation period, the off time can be 0.5 to 2.0 times longer than the on time. This would reduce MAP rise. Once habituation to the MAP rise occurs, the on-time can be increased to greater than about 60 seconds, but the duty cycle should in some embodiments remain less than about 50%.

Sometimes it may be desirable to activate all fiber types (A, B and C) of the splanchnic nerve. This can be done by increasing the stimulation intensity to levels 8-12× the muscle twitch threshold prior to habituation. The pulse width can preferably be set to a level of 0.250 mSec or greater. Representative parameters can be these:

Current amplitude>2.0 mAmp
Pulse width>0.250 mSec
Frequency 10-20 Hz
On-time<60 seconds
Off-time>60 seconds Similarly, the on time can be reduced to a longer period, keeping the duty cycle between 10 and 50%, once habituation occurred in this parameter.

It should be noted that the current amplitude will vary depending on the type of electrode used. A helical electrode that has intimate contact with the nerve will have a lower amplitude than a cylindrical electrode that may reside millimeters away from the nerve. In general, the current amplitude used to cause stimulation is proportional to 1/(radial distance from nerve)$^2$. The pulse width can remain constant or can be increased to compensate for the greater distance. The stimulation intensity would be adjusted to activate the afferent/efferent B or C fibers depending on the electrodes used. Using the muscle-twitching threshold prior to habituation can help guide therapy, given the variability of contact/distance between the nerve and electrode.

We have found that weight loss induced by electrical activation of the splanchnic nerve can be optimized by providing intermittent therapy, or intervals of electrical stimulation followed by intervals of no stimulation. Our data show that after an interval of stimulation, weight loss can be accelerated by turning the stimulation off. This is directly counter to the notion that termination of therapy would result in a rebound phenomenon of increased food intake and weight gain. These data also indicate that a dynamic, or changing, stimulation intensity (e.g., increasing or decreasing daily) produces a more pronounced weight loss than stimulation at a constant intensity. Given these two findings, two dosing strategies are described below.

These treatment algorithms are derived from studies involving canines. The muscle twitch threshold using a helical electrode is determined after adequate healing time post implant has elapsed (2-6 weeks). This threshold may range from about 0.125 mAmp-mSec to about 0.5 mAmp-mSec. The stimulation intensity is increased daily over 1-2 weeks, allowing some or complete habituation to muscle twitching to occur between successive increases, until an intensity of 8-10× the muscle twitch threshold is achieved (1.0-5.0 mAmp-sec). During this period, a rapid decline in body weight and food intake is observed. After the initial weight loss period, a transition period is observed over 1-4 weeks in which some lost weight may be regained. Subsequently, a sustained, gradual reduction in weight and food intake occurs during a prolonged a stimulation phase of 4-8 weeks. After this period of sustained weight loss, the stimulation may be terminated, which is again followed by a steep decline in weight and food intake, similar to the initial stimulation intensity ramping phase. The post-stimulation weight and food decline may last for 1-4 weeks, after which the treatment algorithm can be repeated to create a therapy cycle, or intermittent treatment interval, that results in sustained weight loss. The duty cycle during this intermittent therapy may range from 20-50% with stimulation on-times of up to 15-60 seconds. This intermittent therapy not only optimizes the weight loss, but also extends the battery life of the implanted device.

In another intermittent therapy treatment algorithm embodiment, therapy cycling occurs during a 24-hour period. In this algorithm, the stimulation intensity is maintained at 1×-3× the muscle twitch threshold for a 12-18 hour period. Alternatively, the stimulation intensity can be increased gradually (e.g., each hour) during the first stimulation interval. The stimulation is subsequently terminated for 6-12 hours. Alternatively, the stimulation intensity can be gradually decreased during the second interval back to the muscle twitch threshold level. Due to this sustained or accelerating effect that occurs even after cessation of stimulation, the risk of binge eating and weight gain during the off period or declining stimulation intensity period is minimized.

Alternatively, an alpha-sympathetic receptor blocker, such as prazosin, can be used to blunt the rise in MAP. Alpha-blockers are commonly available antihypertensive medications. The rise in MAP seen with splanchnic nerve stimulation is the result of alpha-receptor activation, which mediates arterial constriction. Because the affects of this therapy on reduced food intake and energy expenditure are related to beta-sympathetic receptor activity, addition of the alpha-blocker would not likely alter the therapeutic weight loss benefits.

Figure 11A:
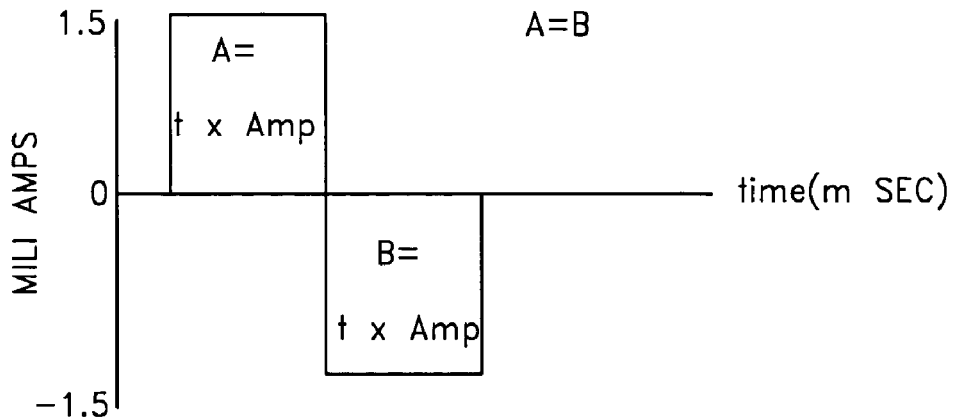
FIGS. 11a and 11b are graphs of electrical signal waveforms.
Figure 11B:
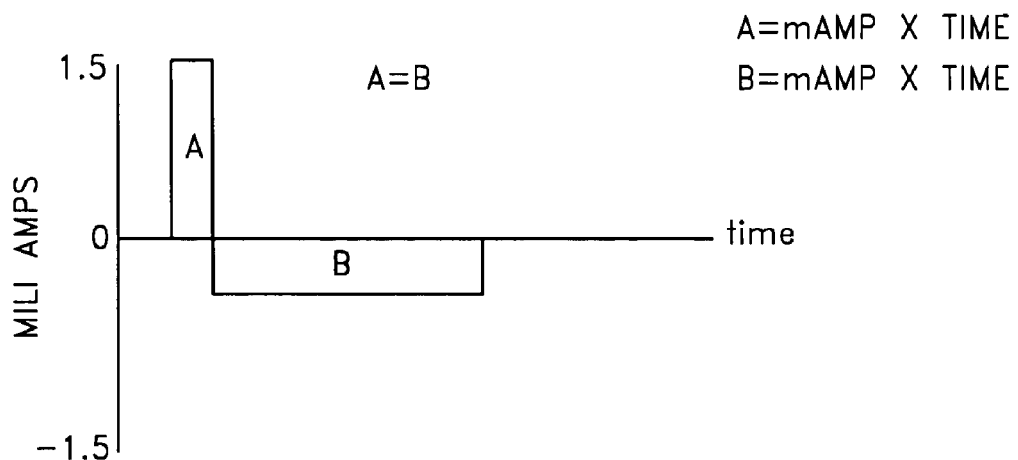

In one embodiment a helical electrode design with platinum iridium ribbon electrodes is used. The electrodes encircle all or a substantial portion of the nerve. A balanced charge biphasic pulse is be delivered to the electrodes, resulting in a bidirectional action potential to activate both efferent and afferent neurons. However, utilizing a waveform that is asymmetrical between the positive and negative phase deflections can create a unidirectional action potential, resulting in anodal block without incidental afferent fiber activation. Thus, whereas a typical biphasic waveform has equal positive and negative phase deflections (FIG. 11a), the anodal blocking waveform would have a short and tall positive deflection followed by a long shallow negative deflection (FIG. 11b). The amperage X time for each deflection would be equal thereby achieves a charge balance. Charge balance is a consideration for avoiding nerve damage.

Figure 12:
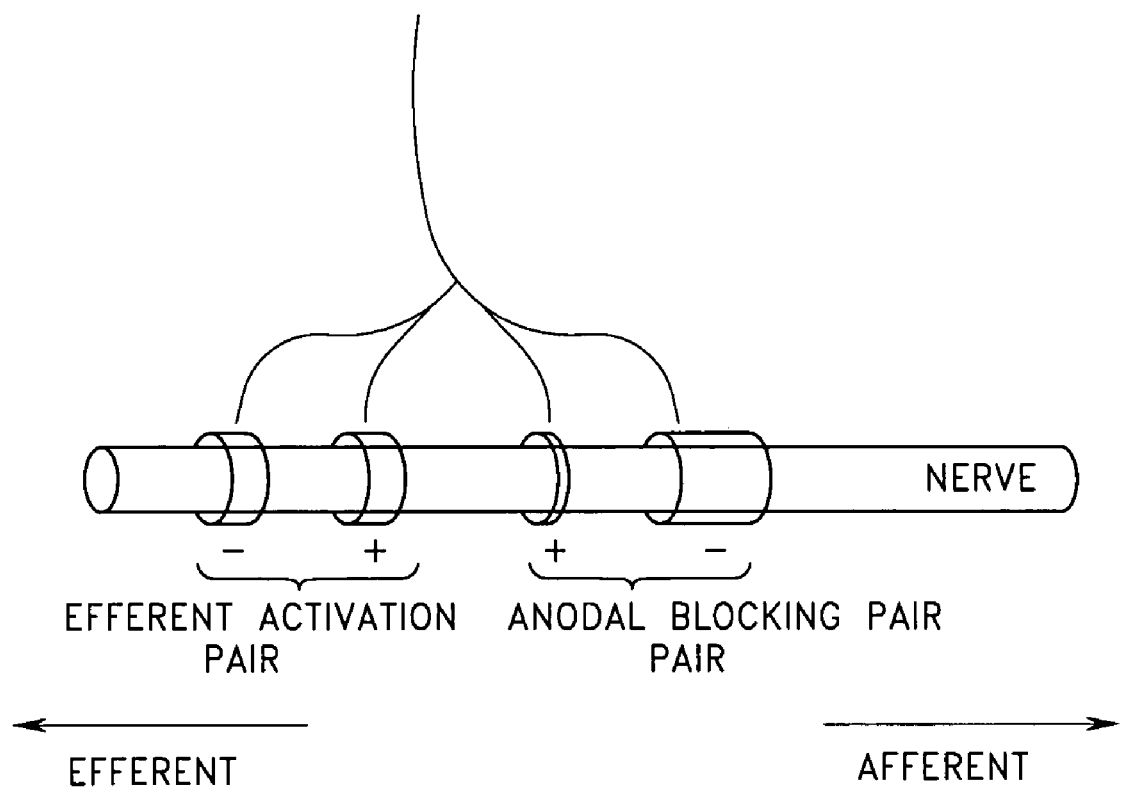
FIG. 12 is a schematic lateral view of an electrode assembly.
Figure 13:
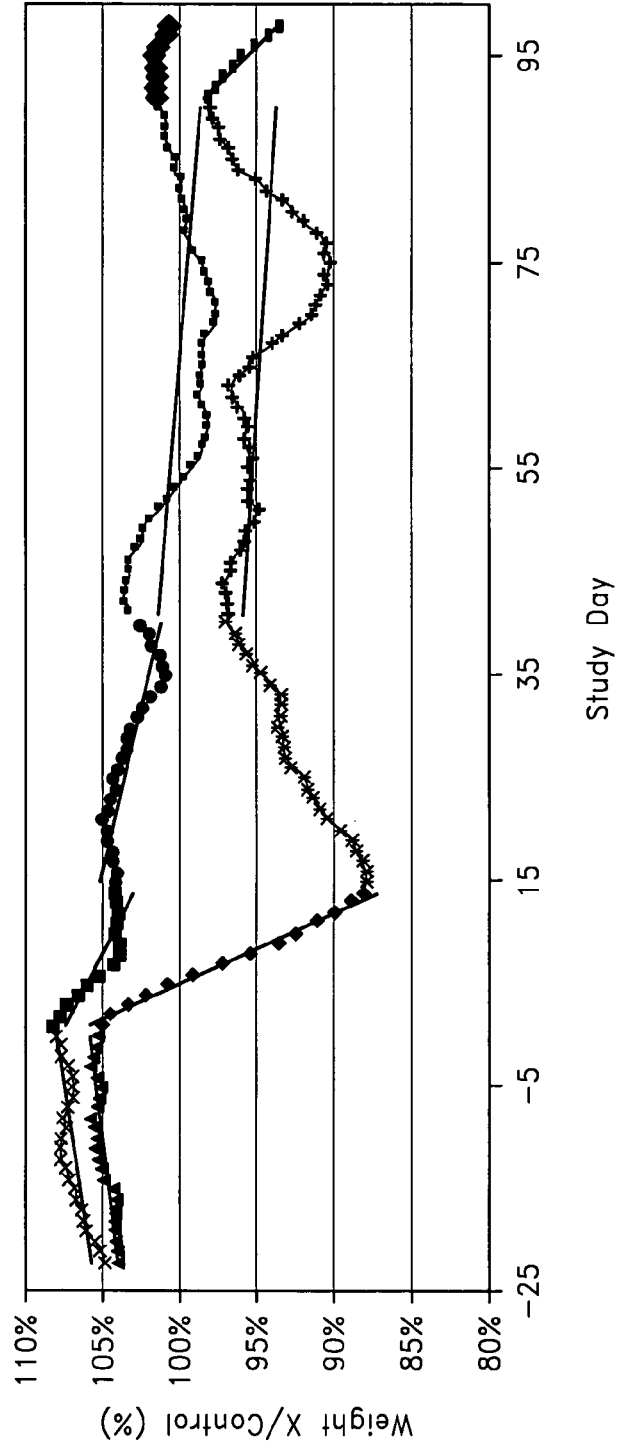
FIG. 13 shows a rolling seven-day average of animal weight.

Alternatively, a quadripolar electrode assembly can be used. One pair of electrode placed distally on the nerve would be used to produce efferent nerve activation. The second proximal pair would be used to block the afferent A fiber conduction. The blocking electrode pair can have asymmetric electrode surface areas, with the cathode surface area being greater than the anode (described by Petruska, U.S. Pat. No. 5,755,750) (FIG. 12). Because of the large surface area at the cathode, the charge density would be insufficient to cause activation. The small surface area at the anode would cause hyperpolarization, particularly in the A fibers, and thereby block afferent conduction. Signals can be sent to four electrodes, timed such that when the efferent activation pair created a bi-directional action potential, the blocking pair would be active as the afferent potential traveled up the nerve. Alternatively, the blocking pair can be activated continuously during the treatment period.

A tripolar electrode can also be used to get activation of a select fiber size bilaterally or to get unilateral activation. To get bi-directional activation of B fibers and anodal blocking of A fibers, a tripolar electrode with the cathode flanked proximally and distally by anodes would be used. Unidirectional activation would be achieved by moving the cathode closer to the proximal electrode and delivering differential current ratios to the anodes.

Pulse generation for electrical nerve modulation is accomplished using a pulse generator. Pulse generators can use microprocessors and other standard electrical components. A pulse generator for this embodiment can generate a pulse, or energy signal, at frequencies ranging from approximately 0.5 Hz to approximately 300 Hz, a pulse width from approximately 10 to approximately 1,000 microseconds, and a constant current of between approximately 0.1 milliamperes to approximately 20 milliamperes. The pulse generator can be capable of producing a ramped, or sloped, rise in the current amplitude. The preferred pulse generator can communicate with an external programmer and or monitor. Passwords, handshakes and parity checks are employed for data integrity. The pulse generator can be battery operated or operated by an external radiofrequency device. Because the pulse generator, associated components, and battery can be implanted, they are, in some embodiments, preferably encased in an epoxy-titanium shell.

Figure 5:
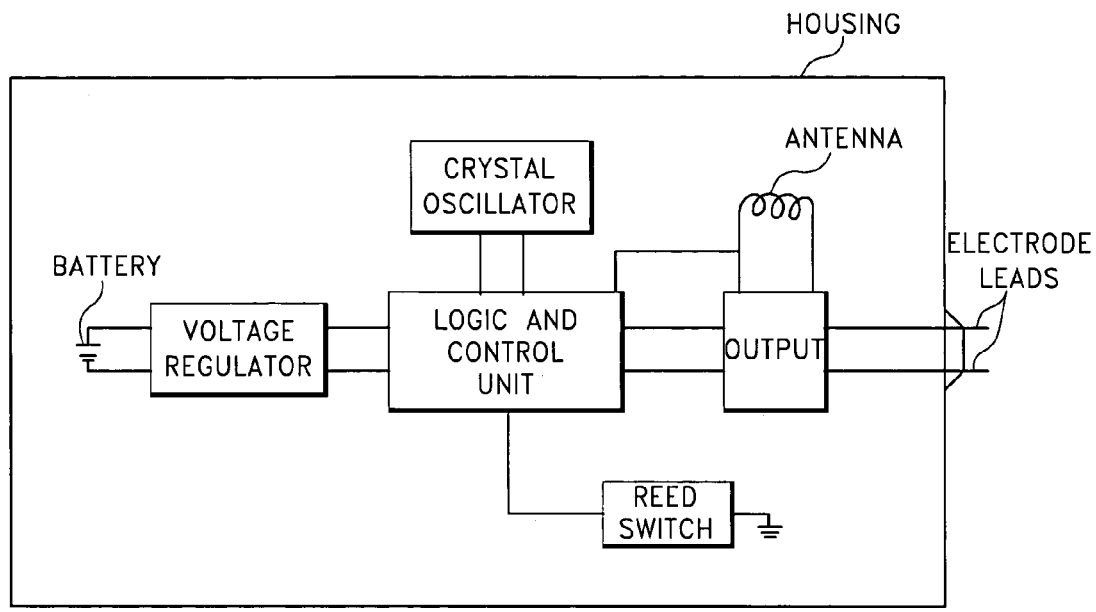
FIG. 5 is a schematic of an exemplary pulse generator.

A schematic of the implantable pulse generator (IPG) is shown in FIG. 5. Components are housed in the epoxy-titanium shell. The battery supplies power to the logic and control unit. A voltage regulator controls the battery output. The logic and control unit control the stimulus output and allow for programming of the various parameters such as pulse width, amplitude, and frequency. In addition, the stimulation pattern and treatment parameters can be programmed at the logic and control unit. A crystal oscillator provides timing signals for the pulse and for the logic and control unit. An antenna is used for receiving communications from an external programmer and for status checking the device. The programmer would allow the physician to program the required stimulation intensity increase to allow for muscle and MAP habituation for a given patient and depending on the treatment frequency. Alternatively, the IPG can be programmed to increase the stimulation intensity at a set rate, such as 0.1 mAmp each hour at a pulse width of 0.25-0.5 mSec. The output section can include a radio transmitter to inductively couple with the wireless electrode to apply the energy pulse to the nerve. The reed switch allows manual activation using an external magnet. Devices powered by an external radiofrequency device would limit the components of the pulse generator to primarily a receiving coil or antenna. Alternatively, an external pulse generator can inductively couple via radio waves directly with a wireless electrode implanted near the nerve.

The IPG is coupled to a lead (where used) and an electrode. The lead (where used) is a bundle of electrically conducting wires insulated from the surroundings by a non-electrically conducting coating. The wires of the lead connect the IPG to the stimulation electrodes, which transfers the energy pulse to the nerve. A single wire can connect the IPG to the electrode, or a wire bundle can connect the IPG to the electrode. Wire bundles may or may not be braided. Wire bundles are preferred because they increase reliability and durability. Alternatively, a helical wire assembly can be utilized to improve durability with flexion and extension of the lead.

Figure 6:
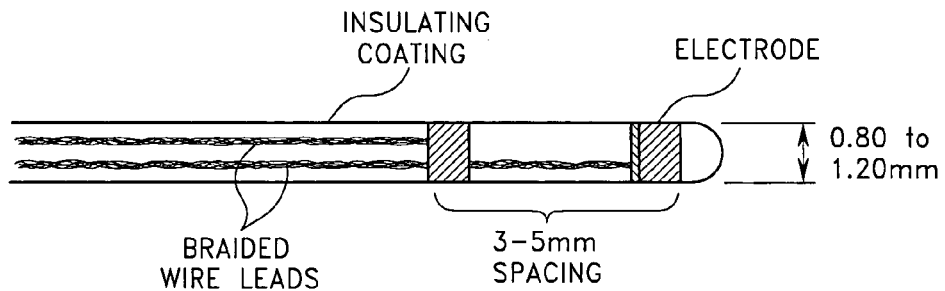
FIG. 6 is a diagram of an exemplary catheter-type lead and electrode assembly.

The electrodes are preferably platinum or platinum-iridium ribbons or rings as shown in FIG. 6. The electrodes are capable of electrically coupling with the surrounding tissue and nerve. The electrodes can encircle a catheter-like lead assembly. The distal electrode can form a rounded cap at the end to create a bullet nose shape. Preferably, this electrode serves as the cathode. A lead of this type can contain 2 to 4 ring electrodes spaced anywhere from 2.0 to 5.0 mm apart with each ring electrode being approximately 1.0 to approximately 10.0 mm in width. Catheter lead electrode assemblies may have an outer diameter of approximately 0.5 mm to approximately 1.5 mm to facilitate percutaneous placement using an introducer.

Alternatively a helical or cuff electrode is used, as are known to those of skill in the art. A helical or cuff electrode can prevent migration of the lead away from the nerve. Helical electrodes may be optimal in some settings because they may reduce the chance of nerve injury and ischemia.

The generator may be implanted subcutaneously, intraabdominally, or intrathoracically, and/or in any location that is appropriate as is known to those of skill in the art.

Alternatively, a wireless system can be employed by having an electrode that inductively couples to an external radiofrequency field. A wireless system would avoid problems such as lead fracture and migration, found in wire-based systems. It would also simplify the implant procedure, by allowing simple injection of the wireless electrode in proximity to the splanchnic nerve, and avoiding the need for lead anchoring, tunneling, and subcutaneous pulse generator implantation.

A wireless electrode would contain a coil/capacitor that would receive a radiofrequency signal. The radiofrequency signal would be generated by a device that would create an electromagnetic field sufficient to power the electrode. It would also provide the desired stimulation parameters (frequency, pulse width, current amplitude, signal on/off time, etc.) The radiofrequency signal generator can be worn externally or implanted subcutaneously. The electrode would also have metallic elements for electrically coupling to the tissue or splanchnic nerve. The metallic elements can be made of platinum or platinum-iridium. Alternatively, the wireless electrode can have a battery that would be charged by an radiofreqency field that would then provide stimulation during intervals without an radiofrequency field.

Bipolar stimulation of a nerve can be accomplished with multiple electrode assemblies with one electrode serving as the positive node and the other serving as a negative node. In this manner nerve activation can be directed primarily in one direction (unilateral), such as efferently, or away from the central nervous system. Alternatively, a nerve cuff electrode can be employed. Helical cuff electrodes as described in U.S. Pat. No. 5,251,634 to Weinberg are preferred. Cuff assemblies can similarly have multiple electrodes and direct and cause unilateral nerve activation.

Unipolar stimulation can also be performed. As used herein, unipolar stimulation means using a single electrode on the lead, while the metallic shell of the IPG, or another external portion of the IPG, functions as a second electrode, remote from the first electrode. This type of unipolar stimulation can be more suitable for splanchnic nerve stimulation than the bipolar stimulation method, particularly if the electrode is to be placed percutaneously under fluoroscopic visualization. With fluoroscopically observed percutaneous placement, it may not be possible to place the electrodes adjacent the nerve, which can be preferred for bipolar stimulation. With unipolar stimulation, a larger energy field is created in order to couple electrically the electrode on the lead with the remote external portion of the IPG, and the generation of this larger energy field can result in activation of the nerve even in the absence of close proximity between the single lead electrode and the nerve. This allows successful nerve stimulation with the single electrode placed in "general proximity" to the nerve, meaning that there can be significantly greater separation between the electrode and the nerve than the "close proximity" used for bipolar stimulation. The magnitude of the allowable separation between the electrode and the nerve will necessarily depend upon the actual magnitude of the energy field that the operator generates with the lead electrode in order to couple with the remote electrode.

In multiple electrode lead assemblies, some of the electrodes can be used for sensing nerve activity. This sensed nerve activity can serve as a signal to commence stimulation therapy. For example, afferent action potentials in the splanchnic nerve, created due to the commencement of feeding, can be sensed and used to activate the IPG to begin stimulation of the efferent neurons of the splanchnic nerve. Appropriate circuitry and logic for receiving and filtering the sensed signal would be used in the IPG.

Because branches of the splanchnic nerve directly innervate the adrenal medulla, electrical activation of the splanchnic nerve results in the release of catecholamines (epinephrine and norepinephrine) into the blood stream. In addition, dopamine and cortisol, which also raise energy expenditure, can be released. Catecholamines can increase energy expenditure by about 15% to 20%. By comparison, subitramine, a pharmacologic agent used to treat obesity, increases energy expenditure by approximately only 3% to 5%.

Figure 7:
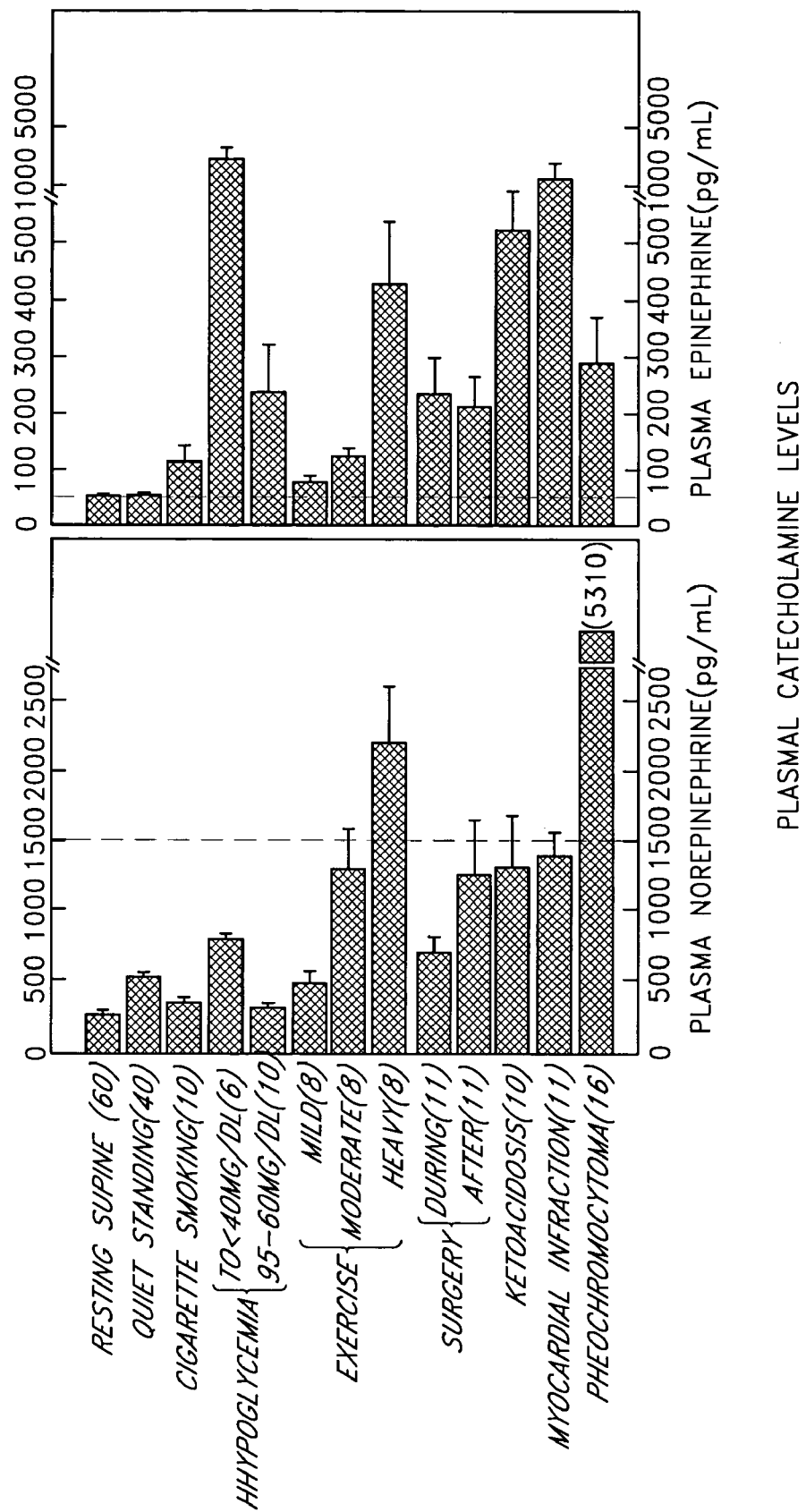
FIG. 7 is a graph of known plasma catecholamine levels in various physiologic and pathologic states.

Human resting venous blood levels of norepinephrine and epinephrine are approximately 25 picograms (pg)/milliliter (ml) and 300 pg/ml, respectively, as shown in FIG. 7. Detectable physiologic changes such as increased heart rate occur at norepinephrine levels of approximately 1,500 pg/ml and epinephrine levels of approximately 50 pg/ml. Venous blood levels of norepinephrine can reach as high 2,000 pg/ml during heavy exercise, and levels of epinephrine can reach as high as 400 to 600 pg/ml during heavy exercise. Mild exercise produces norepinephrine and epinephrine levels of approximately 500 pg/ml and 100 pg/ml, respectively. It can be desirable to maintain catecholamine levels somewhere between mild and heavy exercise during electrical sympathetic activation treatment for obesity.

Figure 8A:
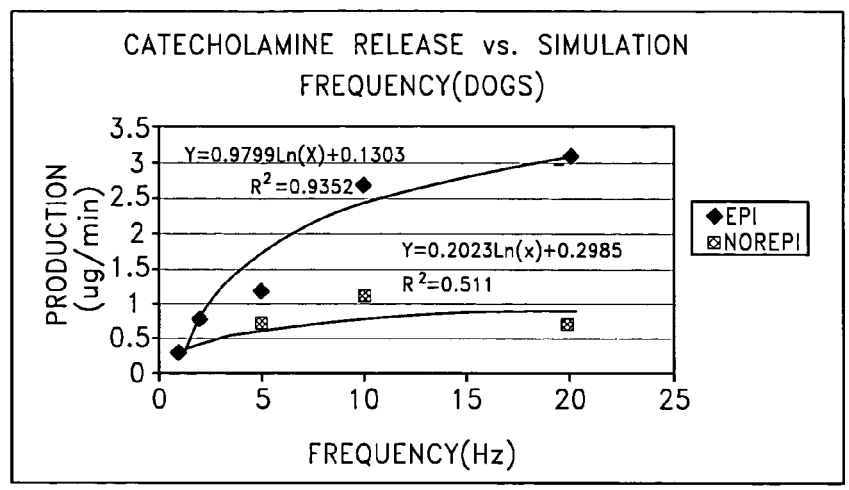
FIGS. 8a, 8b, and 8c are exemplary graphs of the effect of splanchnic nerve stimulation on catecholamine release rates, epinephrine levels, and energy expenditure, respectively.
Figure 8B:
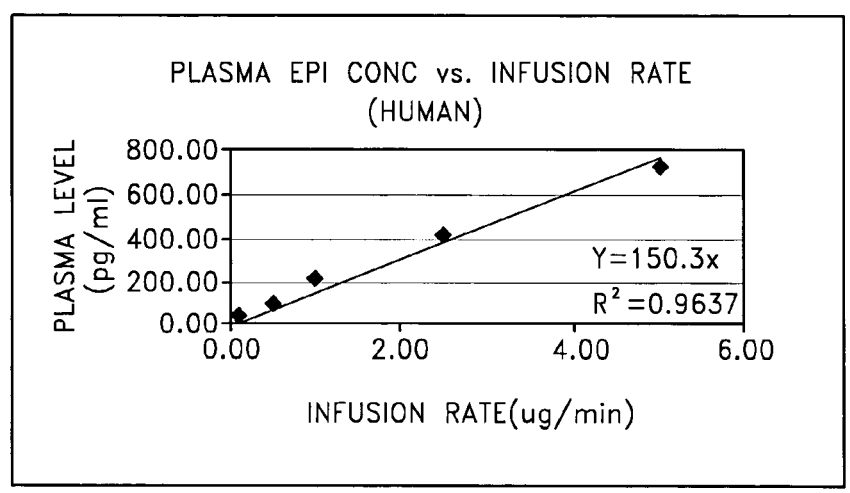
Figure 8C:
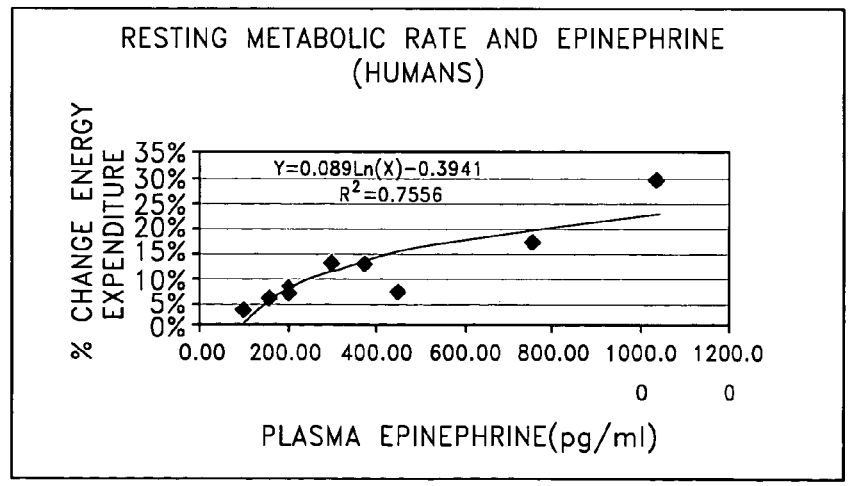

In anesthetized animals, electrical stimulation of the splanchnic nerve has shown to raise blood catecholamine levels in a frequency dependent manner in the range of about 1 Hz to about 20 Hz, such that rates of catecholamine release/production of 0.3 to 4.0 μg/min can be achieved. These rates are sufficient to raise plasma concentrations of epinephrine to as high as 400 to 600 pg/ml, which in turn can result in increased energy expenditure from 10% to 20% as shown in FIG. 8. During stimulation, the ratio of epinephrine to norepinephrine is 65% to 35%. One can change the ratio by stimulating at higher frequencies. In some embodiments this is desired to alter the energy expenditure and/or prevent a rise in MAP.

Energy expenditure in humans ranges from approximately 1.5 kcal/min to 2.5 kcal/min. A 15% increase in this energy expenditure in a person with a 2.0 kcal/min energy expenditure would increase expenditure by 0.3 kcal/min. Depending on treatment parameters, this can result in an additional 100 to 250 kcal of daily expenditure and 36,000 to 91,000 kcal of yearly expenditure. One pound of fat is 3500 kcal, yielding an annual weight loss of 10 to 26 pounds.

Increased energy expenditure would is fueled by fat and carbohydrate metabolism. Postganglionic branches of the splanchnic nerve innervate the liver and fat deposits of the abdomen. Activation of the splanchnic nerve can result in fat metabolism and the liberation of fatty acids, as well as glycogen breakdown and the release of glucose from the liver. Fat metabolism coupled with increased energy expenditure can result in a net reduction in fat reserves.

Figure 9:
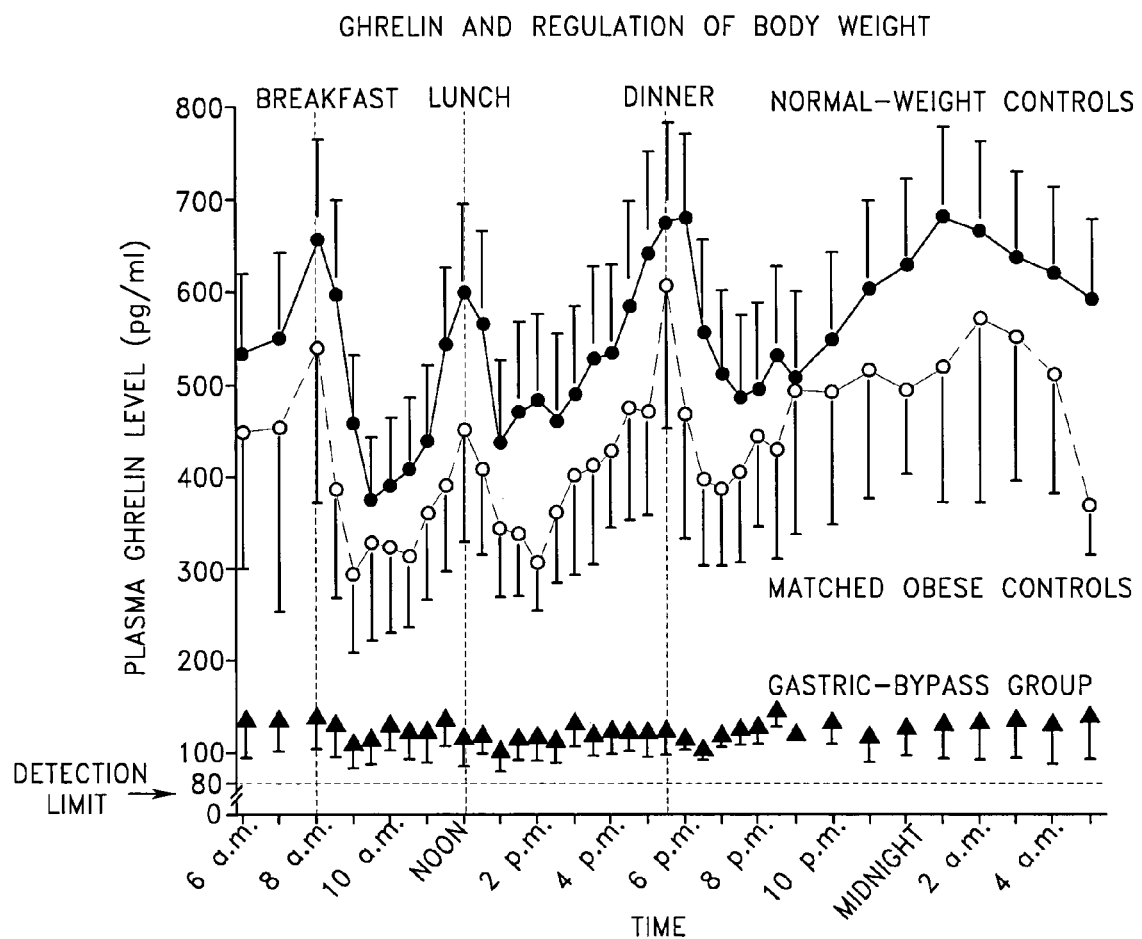
FIG. 9 is a graph of known plasma ghrelin levels over a daily cycle, for various subjects.
Figure 14:
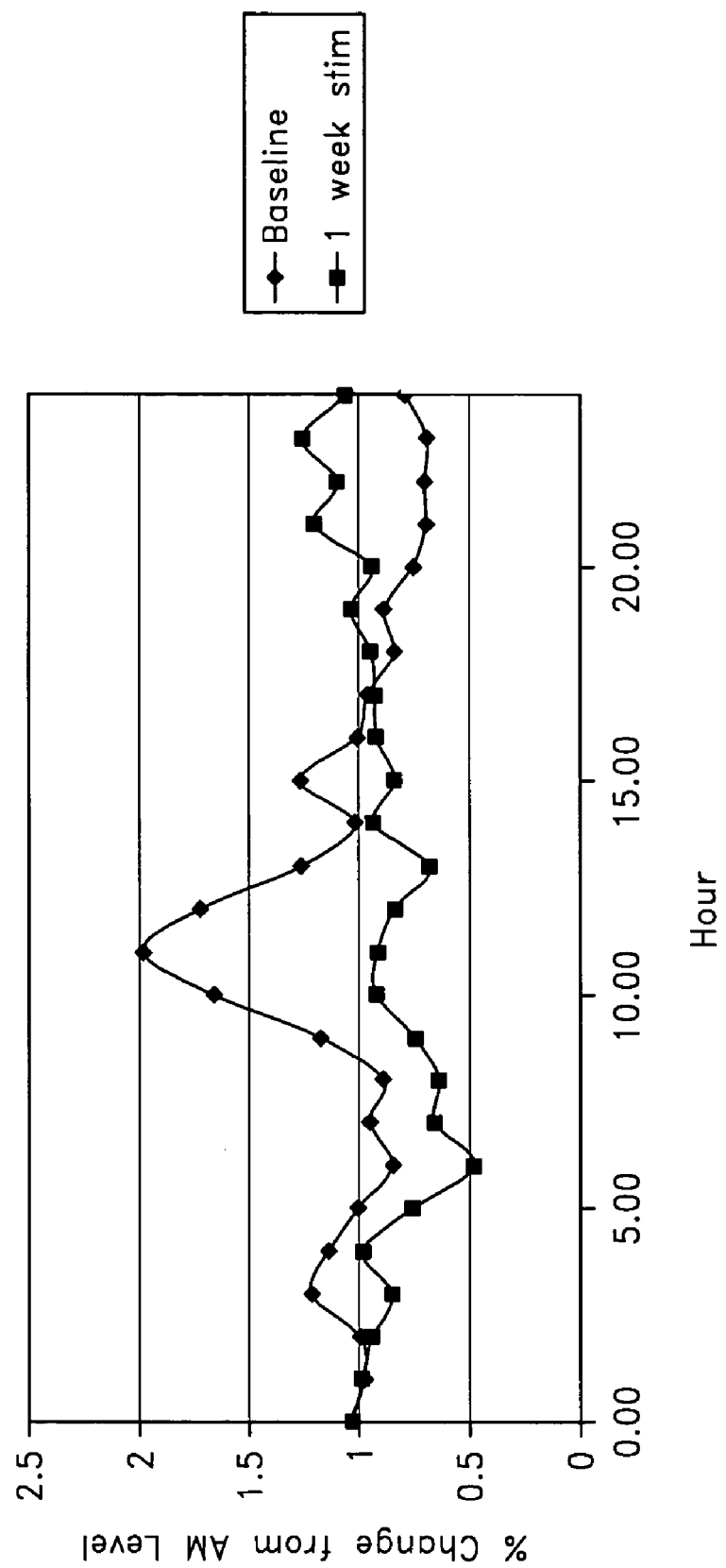
FIG. 14 shows plasma ghrelin levels before and after splanchnic nerve stimulation.

In some embodiments, it may be desirable to titrate obesity therapy to plasma ghrelin levels. In humans, venous blood ghrelin levels range from approximately 250 pg/ml to greater than 700 pg/ml as shown in FIG. 9. Ghrelin levels rise and fall during the day with peak levels typically occurring just before meals. Ghrelin surges are believed to stimulate appetite and lead to feeding. Surges in ghrelin may be as high as 1.5-2.0 times that of basal levels. The total ghrelin production in a 24-hour period is believed to be related to the energy state of the patient. Dieting that results in a state of energy deficit is associated with a higher total ghrelin level in a 24-hour period. Splanchnic nerve stimulation has been shown to eliminate or substantially reduce ghrelin surges or spikes. In a canine model, ghrelin levels prior to splanchnic nerve stimulation showed a midday surge of almost 2.0 times basal levels. After one week of stimulation at 20 Hz, on-time of approximately 60 seconds, off-time of approximately 120 seconds, and a peak current intensity of 8× the muscle twitch threshold, this midday surge was almost eliminated (FIG. 14). In addition, it increased the total ghrelin production in a 24-hour period, reflecting an energy-deficient state (baseline area under the curve=$64.1 \times 10^4$, stimulation area under the curve=$104.1 \times 10^4$). Splanchnic nerve activation, in the treatment of obesity, can be titrated to reduce ghrelin surges and attain the desired energy deficit state for optimal weight loss. Reductions in food intake comparable to the increases in energy expenditure (i.e. 100 to 250 kcal/day) can yield a total daily kcal reduction of 200 to 500 per day, and 20 to 50 pounds of weight loss per year.

In anesthetized animals, electrical activation of the splanchnic nerve has also been shown to decrease insulin secretion. In obesity, insulin levels are often elevated, and insulin resistant diabetes (Type II) is common. Down-regulation of insulin secretion by splanchnic nerve activation may help correct insulin resistant diabetes.

Figure 10:
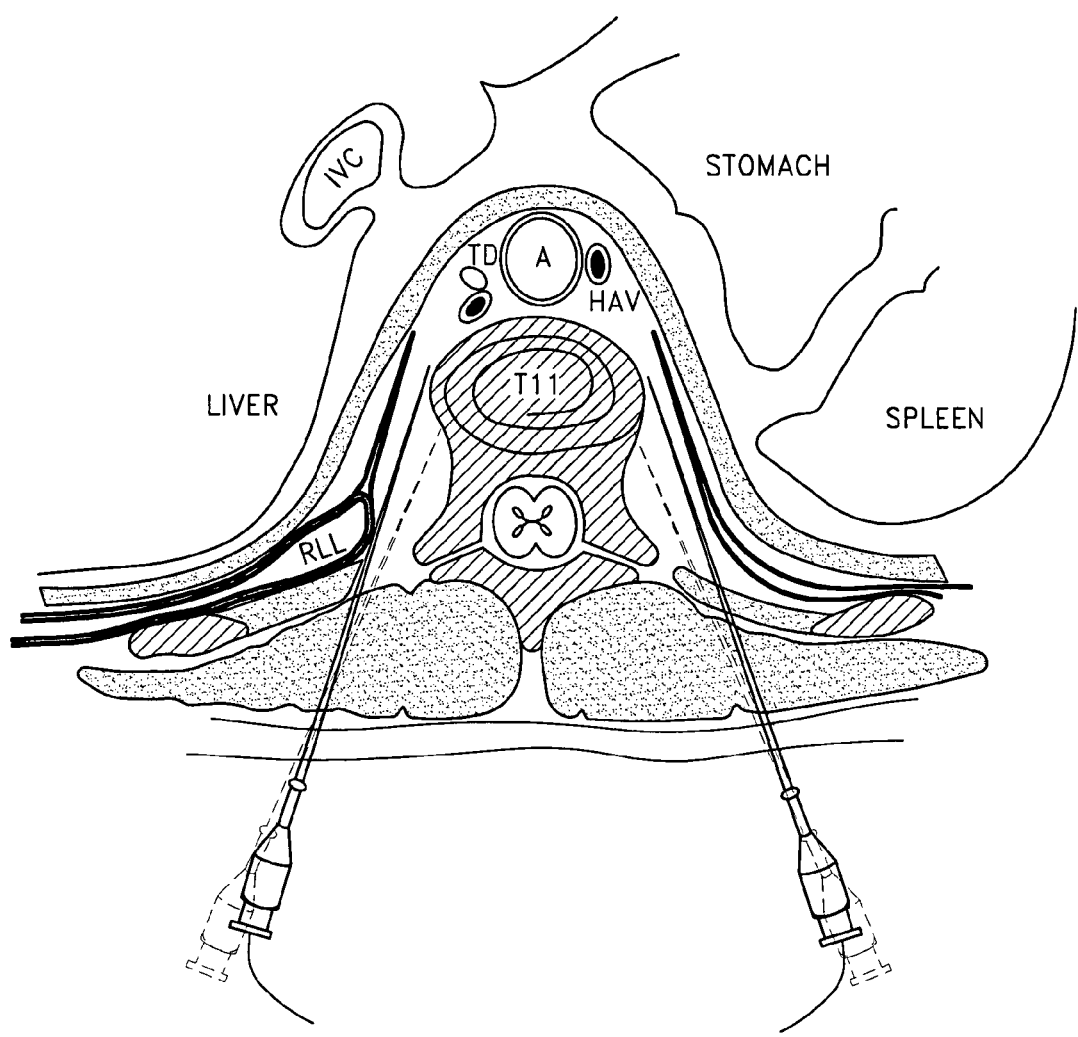
FIG. 10 is a section view of an exemplary instrument placement, for implantation of an electrode assembly.

Implantation of the lead/electrode assembly for activation of the greater splanchnic nerve is preferably accomplished percutaneously using an introducer as shown in FIG. 10. The introducer can be a hollow needle-like device that would be placed posteriorly through the skin between the ribs paramidline at the T9-T12 level of the thoracic spinal column. A posterior placement with the patient prone is preferred to allow bilateral electrode placement at the splanchnic nerves, if desired. Placement of the needle can be guided using fluoroscopy, ultrasound, or CT scanning. Proximity to the splanchnic nerve by the introducer can be sensed by providing energy pulses to the introducer electrically to activate the nerve while monitoring for a rise in MAP or muscle twitching. All but the tip of the introducer can be electrically isolated so as to focus the energy delivered to the tip of the introducer. The lower the current amplitude used to cause a rise in the MAP or muscle twitch, the closer the introducer tip would be to the nerve. Preferably, the introducer tip serves as the cathode for stimulation. Alternatively, a stimulation endoscope can be placed into the stomach of the patient for electrical stimulation of the stomach. The evoked potentials created in the stomach can be sensed in the splanchnic nerve by the introducer. To avoid damage to the spinal nerves, the introducer can sense evoked potentials created by electrically activating peripheral sensory nerves. Alternatively, evoked potentials can be created in the lower intercostal nerves or upper abdominal nerves and sensed in the splanchnic. Once the introducer was in proximity to the nerve, a catheter type lead electrode assembly would be inserted through the introducer and adjacent to the nerve. Alternatively, a wireless, radiofrequency battery charged, electrode can be advanced through the introducer to reside alongside the nerve. In either case, stimulating the nerve and monitoring for a rise in MAP or muscle twitch can be used to confirm electrode placement.

Once the electrode was in place the current amplitude would be increased at a pulse width of 50 to 500 µsec and a frequency of 1 Hz, until the threshold for muscle twitching was reached. The current amplitude can be set slightly above or slightly below this muscle twitch threshold. After identifying the desired current amplitude the pulse width can be increased by as much as 2.5 times and the frequency increased up to 40 Hz for therapeutic stimulation. The lead (where used) and the IPG would be implanted subcutaneously in the patient's back or side. The lead would be appropriately secured to avoid dislodgement. The lesser and least splanchnic nerves can also be activated to some degree by lead/electrode placement according to the above procedure, due to their proximity to the splanchnic nerve.

Percutaneous placement of the lead electrode assembly can be enhanced using direct or video assisted visualization. An optical port can be incorporated into the introducer. A channel can allow the electrode lead assembly to be inserted and positioned, once the nerve was visualized. Alternatively, a percutaneous endoscope can be inserted into the chest cavity for viewing advancement of the introducer to the nerve. The parietal lung pleura are relatively clear, and the nerves and introducer can be seen running along the vertebral bodies. With the patient prone, the lungs are pulled forward by gravity creating a space for the endoscope and for viewing. This can avoid the need for single lung ventilation. If desired, one lung can be collapsed to provide space for viewing. This is a common and safe procedure performed using a bifurcated endotracheal tube. The endoscope can also be placed laterally, and positive $CO_2$ pressure can be used to push down the diaphragm, thereby creating a space for viewing and avoiding lung collapse.

Alternatively, stimulation electrodes can be placed along the sympathetic chain ganglia from approximately vertebra T4 to T11. This implantation can be accomplished in a similar percutaneous manner as above. This would create a more general activation of the sympathetic nervous system, though it would include activation of the neurons that comprise the splanchnic nerves.

Alternatively, the lead/electrode assembly can be placed intra-abdominally on the portion of the splanchnic nerve that resides retroperitoneally on the abdominal aorta just prior to synapsing in the celiac ganglia. Access to the nerve in this region can be accomplished laparoscopically, using typical laparoscopic techniques, or via open laparotomy. A cuff electrode can be used to encircle the nerve unilaterally or bilaterally. The lead can be anchored to the crus of the diaphragm. A cuff or patch electrode can also be attached to the celiac ganglia unilaterally or bilaterally. Similar activation of the splanchnic branches of the sympathetic nervous system would occur as implanting the lead electrode assembly in the thoracic region.

An alternative lead/electrode placement would be a transvascular approach. Due to the proximity of the splanchnic nerves to the azygous veins shown in FIG. 10, and in particular the right splanchnic nerve and right azygous vein, modulation can be accomplished by positioning a lead/electrode assembly in this vessel. Access to the venous system and azygous vein can occur via the subclavian vein using standard techniques. The electrode/lead assembly can be mounted on a catheter. A guidewire can be used to position the catheter in the azygous vein. The lead/electrode assembly would include an expandable member, such as a stent. The electrodes would be attached to the stent, and using balloon dilation of the expandable member, can be pressed against the vessel wall so that energy delivery can be transferred to the nerve. The expandable member would allow fixation of the electrode lead assembly in the vessel. The IPG and remaining lead outside of the vasculature would be implanted subcutaneously in a manner similar to a heart pacemaker.

In some embodiments, the apparatus for nerve stimulation can be shielded or otherwise made compatible with magnetic resonance imaging (MRI) devices, such that the apparatus is less susceptible to the following effects during exposure to magnetic fields: (a) current induction and its resultant heat effects and potential malfunction of electronics in the apparatus, and (b) movement of the apparatus due to Lorentz forces. This type of magnetic shielding can be accomplished by, for example, using materials for the generator and/or electrode that are nanomagnetic or utilize carbon composite coatings. Such techniques are described in U.S. Pat. Nos. 6,506,972 and 6,673,999, and U.S. patent application Ser. No. 2002/0183796, published Dec. 5, 2002; U.S. patent application Ser. No. 2003/0195570, published Oct. 16, 2003; and U.S. patent application Ser. No. 2002/0147470, published Oct. 10, 2002. The entireties of all of these references are hereby incorporated by reference.

For purposes of summarizing the invention, certain aspects, advantages, and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A method for treating a medical condition, the method comprising:
    electrically coupling an electrode to a splanchnic nerve in a mammal at a location above the diaphragm of the mammal;
    electrically activating the splanchnic nerve, wherein the electrically activating is performed in a stimulation pattern for a first time period within a period of about 24 hours; and
    ceasing the electrical activation of the splanchnic nerve for a second time period within the period of about 24 hours,
    wherein the stimulation pattern includes a stimulation intensity pattern adapted and configured to result in net weight loss in the mammal over a period of about 4 to 8 weeks.

2. The method of claim 1, further comprising repeating the steps of electrically activating and ceasing the electrical activation.

3. The method of claim 1, wherein the first time period plus the second time period equals about 24 hours.

4. The method of claim 1, further comprising varying the stimulation intensity over time.

5. The method of claim 1, further comprising increasing the stimulation intensity daily.

6. The method of claim 1, further comprising creating a unidirectional action potential in the splanchnic nerve.

7. The method of claim 1, further comprising creating an anodal block in the splanchnic nerve.

8. The method of claim 1, further comprising administering an alpha sympathetic receptor blocker.

9. The method of claim 1, further comprising titrating the electrical activating to the plasma level of a catecholamine achieved during therapy.

10. The method of claim 1, wherein the electrically activating is performed about every three hours, for durations of between about 2 to 30 minutes.

11. The method of claim 1, wherein the electrically activating is delivered at intervals coinciding with meal times.

12. The method of claim 11, wherein the electrically activating lasts from between 1 and 3 hours.

13. The method of claim 11, wherein the electrically activating staffs just prior to the meal.

14. The method of claim 11, wherein the electrically activating staffs as much as one hour before the meal.

15. The method of claim 1, wherein the electrically activating stimulation intensity is increased in a stepwise manner.

16. The method of claim 1, wherein the electrically activating stimulation intensity pattern is configured to result in net sustained weight loss in the mammal over a period of about 95 days.

17. The method of claim 1, in which the stimulation pattern includes increasing the stimulation intensity in increments which allow for habituation to the increased intensity.

18. The method of claim 17, in which the stimulation intensity is incremented by about 0.5 mA daily.

19. The method of claim 1, in which the stimulation pattern includes increasing the stimulation intensity over a plurality of days sufficient to substantially reduce the mammal's weight, and in which the stimulation pattern further includes substantially decreasing the stimulation intensity for a time sufficient to further reduce the mammal's weight, and in which the stimulation pattern includes repeating the increasing and substantially decreasing intensity steps.

20. The method of claim 1, in which the stimulation pattern includes stimulating the nerve over a plurality of days sufficient to substantially reduce the mammal's weight, and in which the stimulation pattern further includes substantially decreasing the stimulation intensity for a time and amount sufficient to further reduce the mammal's weight, and in which the stimulation pattern includes repeating the stimulating the nerve and substantially decreasing intensity steps.

21. The method of claim 20, in which the stimulation intensity is initially adjusted based on muscle twitch observations.

* * * * *

UNITED STATES PATENT AND TRADEMARK OFFICE
CERTIFICATE OF CORRECTION

PATENT NO. : 7,551,964 B2
APPLICATION NO. : 10/785726
DATED : June 23, 2009
INVENTOR(S) : John D. Dobak, III It is certified that error appears in the above-identified patent and that said Letters Patent is hereby corrected as shown below:

On the title page, under "Other Publications", in column 2, line 1, delete "Gulcagon," and insert -- Glucagon, --, therefor.

On page 2, under "Other Publications", in column 2, line 2, delete "Endocrinolgy" and insert -- Endocrinology --, therefor.

On page 3, under "Other Publications", in column 1, line 17, delete "Hypthalamic" and insert -- Hypothalamic --, therefor.

On page 3, under "Other Publications", in column 2, line 5, delete "HCO3" and insert -- $HCO_3$ --, therefor.

On page 3, under "Other Publications", in column 2, line 31, delete "Gylcogenolytic" and insert -- Glycogenolytic --, therefor.

On page 3, under "Other Publications", in column 2, line 35, delete "Activiation," and insert -- Activation, --, therefor.

On page 3, under "Other Publications", in column 2, line 39, delete "Endorinology" and insert -- Endocrinology --, therefor.

On page 4, under "Other Publications", in column 1, line 25, delete "low" and insert -- lower --, therefor.

On page 4, under "Other Publications", in column 2, line 19, delete "Blateral" and insert -- Bilateral --, therefor.

On page 4, under "Other Publications", in column 2, line 53, delete "Splachnic" and insert -- Splanchnic --, therefor.

On page 4, under "Other Publications", in column 2, line 61, delete "Neurosurgey;" and insert -- Neurosurgery; --, therefor.

In column 2, line 19, delete "subitramine," and insert -- sibutramine, --, therefor.

In column 6, line 42, delete "stimulation-pattern" and insert -- stimulation pattern --, therefor.

CERTIFICATE OF CORRECTION (continued)
U.S. Pat. No. 7,551,964 B2

In column 9, line 64, delete "post-ganglionic" and insert -- postganglionic --, therefor.

In column 17, line 62, delete "subitramine," and insert -- sibutramine, --, therefor.

In column 22, line 12, in Claim 13, delete "staffs" and insert -- starts --, therefor.

In column 22, line 14, in Claim 14, delete "staffs" and insert -- starts --, therefor.

Signed and Sealed this

Sixteenth Day of February, 2010

David J. Kappos
*Director of the United States Patent and Trademark Office*